(12) United States Patent
Amsden

(10) Patent No.: US 6,984,393 B2
(45) Date of Patent: Jan. 10, 2006

(54) BIODEGRADABLE ELASTOMER AND METHOD OF PREPARING SAME

(75) Inventor: Brian G. Amsden, Kingston (CA)

(73) Assignee: Queen's University at Kingston, Kingston (CA)

( * ) Notice: Subject to any disclaimer, the term of this patent is extended or adjusted under 35 U.S.C. 154(b) by 518 days.

(21) Appl. No.: 10/139,643

(22) Filed: May 7, 2002

(65) Prior Publication Data
US 2003/0105245 A1 Jun. 5, 2003

Related U.S. Application Data

(60) Provisional application No. 60/288,783, filed on May 7, 2001.

(51) Int. Cl.
*A61F 2/02* (2006.01)
*C08G 69/14* (2006.01)
*C08G 63/08* (2006.01)

(52) U.S. Cl. ............. 424/423; 424/486; 528/196; 528/201; 528/323; 528/354

(58) Field of Classification Search ............ 424/423, 424/486; 528/196, 201, 323, 354
See application file for complete search history.

(56) References Cited

U.S. PATENT DOCUMENTS

| 4,666,978 | A | 5/1987 | Storey et al. |
| 5,047,464 | A | 9/1991 | Pogany et al. |
| 5,543,218 | A | 8/1996 | Bennett et al. |
| 5,889,140 | A | 3/1999 | Watanabe |
| 6,001,891 | A | 12/1999 | Higuchi et al. |
| 6,531,147 | B2 * | 3/2003 | Sawhney et al. ......... 424/426 |

OTHER PUBLICATIONS

Bruin, P., et al., "Design and synthesis of biodegradable poly(ester-urethane) elastomer networks composed of non-toxic building blocks," *Makromol. Chem.* 9:589-594 (1988).
Matsuda, T., et al., "Molecular design of photocurable liquid biodegradable copolymers. 1. Synthesis and photocuring characteristics." *Macromolecules* 33:795-800 (2000).
Mizutani, M., et al., "Photocurable liquid biodegradable copolymers: In vitro hydrolytic degradation behaviors of photocured films of coumarin-endcapped poly ($\epsilon$-caprolactone-co-trimethylene carbonate)." *Biomacromolecules* 3:249-255 (2002).
Mizutani, M., et al., "Liquid, phenylazide-end-capped copolymers of $\epsilon$-caprolactone and trimethylene carbonate: Preparation, photocuring characteristics, and surface layering." *Biomacromolecules* 3:668-675 (2002).
Palmgren, R., et al., "Synthesis of degradable crosslinked polymers based on 1,5-dioxepan-2-one and crossslinker of bis-$\epsilon$-caprolactone type." *Polym. Chem.* 35:1635-1649 (1997).
Schindler, A., et al., "Biodegradable elastomeric polyesters." *Polymer Preprints* 23:111-112 (1982).
Storey, R.F., et al., "Degradable polyruethane networks based on D,L-lactide, glycolide, $\epsilon$-caprolactone, and trimethylene carbonate homopolyester and copolyester triols," *Polymer* 35:830-838 (1994).

(Continued)

Primary Examiner—Carlos A. Azpuru
(74) Attorney, Agent, or Firm—Stephen J. Scribner; Carol Miernicki Steeg

(57) ABSTRACT

This invention relates to thermally crosslinked and photo-crosslinked biodegradable and biocompatible elastomeric polymers. The elastomers can be used for biomedical devices such as needles, stents, catheters, scaffolds for tissue engineering, and implantable drug delivery devices. The photo-crosslinked elastomers are particularly useful for delivery devices for proteins and peptides.

56 Claims, 16 Drawing Sheets

OTHER PUBLICATIONS

Storey, R.F., et al., "Methacrylate-endcapped poly(d,l-lactide-co-trimethylene carbonate) oligomers. Network formation by thermal free-radical curing." *Polymer* 38:6295-6301 (1997).

Aoyagi, T; Miyata, F; and Nagase, Y. Preparation of Cross-linked Allphatic Polyester and Application to Thermoresponsive Material. *Journal of Controlled Release.* (1994) 32: 87-96.

* cited by examiner

BIODEGRADABLE ELASTOMER AND METHOD OF PREPARING SAME

RELATED APPLICATION

This application claims the benefit of the filing date of U.S. Provisional Patent Application No. 60/288,783, filed on May 7, 2001, the disclosure of which is incorporated herein by reference in its entirety.

FIELD OF THE INVENTION

This invention relates to biodegradable/biocompatible elastomers.

BACKGROUND OF THE INVENTION

Star polymers and co-polymers have been prepared using degradable monomers such as D,L-lactide, glycolide, $\epsilon$-caprolactone, $\delta$-valerolactone, dioxanone, dioxepanone, trimethylene carbonate, and cyclic amides such as O-benzyl-L-serine (Schindler et al., *Journal of Polymer Science*; Polymer Chemistry Edition 20:319–326, 1982;. Storey et al., *Polymer* 38(26):6295–6301, 1997; Storey et al., *Polymer* 35(4).830–838, 1994; Bruin et al., *Makromol. Chem.* 9:589–594, 1998; Joziasse et al., *Polymer* 39(2):467–473, 1998; Li et al., *Polymer* 39(18):4421–4427, 1998; Kim et al., *Makromol. Chem.* 194:3229–3236, 1993; Kim et al., *Makromol. Chem.* 193:1623–1631, 1992; Hiljanen-Vainio et al., *Journal of Biomedical Materials Research* 34(1):39–46, 1997). These prepolymers have been thermally crosslinked to form elastomers using diisocyanate linkages (Storey et al., *Polymer* 35(4):830–838, 1994; Bruin et al., *Makromol. Chem.* 9:589–594, 1998) and methacrylate groups on the terminal ends (Storey et al., *Polymer* 38(26):6295–6301, 1997). However, diisocyanate crosslinked elastomers, depending on the diisocyanate used, have several disadvantages where biocompatibility/biodegradability are concerned. For example, they may degrade to potentially toxic compounds, they can only be crosslinked in solution, and they require a potentially carcinogenic solvent in order to achieve a dispersion of the crosslinking agent in the polymer. Also, use of such a solvent requires a further solvent removal step, and any residual solvent may jeopardize the biocompatibility of the material. Methacrylate end-capped star co-polymers have been cured to form elastomers, however, the reaction requires cobalt napthenate as a catalyst in an organic solvent. The catalyst raises concerns about biocompatibility as does the use of a solvent.

U.S. Pat. No. 3,072,680, issued Jan. 8, 1963, describes the synthesis of a number of bis-lactones. These compounds have been used to prepare elastomers by co-polymerization with monomers such as caprolactone and other lactones (U.S. Pat. No. 4,379,138, issued Apr. 5, 1983) and dioxepanone (Palmgren et al., *J. Polym. Sci. A: Polym Chem.* 35:1635–1649, 1997). This type of co-polymerization produces a random co-polymer whose crosslinks are strictly tetrafunctional. As this procedure provides little control over the structure of the prepolymers, there is high batch-to-batch variation in the characteristics of the resulting elastomers, making the physical properties and degradation kinetics of the elastomers difficult to reproduce.

Photo-crosslinking has been used to prepare elastomeric materials from acrylate tipped star polyurethanes (U.S. Pat. No. 5,674,921, issued Oct. 7, 1997). However, these urethanes are composed of monomers which produce toxic degradation products. Lactone star co-polymers composed of $\epsilon$-caprolactone and trimethylene carbonate end tipped with coumarin (Matsuda et al., *Macromolecules* 33:795–800, 2000) have been crosslinked using long wave UV light, however these materials are rigid and brittle.

SUMMARY OF THE INVENTION

In accordance with one aspect of the invention there is provided a method of preparing a thermally crosslinked biodegradable/biocompatible elastomeric polymer comprising: combining a star co-polymer with a bis-lactone crosslinking agent, and heating the combined star co-polymer and crosslinking agent, so that a crosslinked biodegradable/biocompatible elastomeric polymer is prepared. According to the invention, the star co-polymer comprises at least one monomer, said at least one monomer capable of forming a biodegradable linkage to another monomer, and an initiator. According to one embodiment, the star co-polymer is capable of undergoing ring-opening polymerization. Preferably, said at least one monomer is a member of a group selected from lactones, carbonates, and cyclic amides. The initiator can be any polyol such as glycerol, pentaerythritol, and xylitol. In one embodiment, the star polymer is a lactone star co-polymer. In further embodiments, the lactone star copolymer comprises $\epsilon$-caprolactone and D,L-lactide. Preferably, the bis-lactone crosslinking agent is (2,2-)bis($\epsilon$-caprolactone-4-yl)propane (BCP).

In accordance with another aspect of the invention there is provided a method of preparing a photo-crosslinked biodegradable/biocompatible elastomeric polymer comprising: combining a photo-crosslinkable star co-polymer with an initiator, and exposing the combined star co-polymer and initiator to photo-crosslinking light; so that a crosslinked biodegradable/biocompatible elastomeric polymer is prepared. According to the invention, the star co-polymer comprises at least one monomer, said at least one monomer capable of forming a biodegradable linkage to another monomer, and one or more photo-crosslinkable groups on the polymer chain termini. According to one embodiment, the star co-polymer is capable of undergoing ring-opening polymerization. Preferably, said at least one monomer is a member of a group selected from lactones, carbonates, and cyclic amides. In accordance with this aspect of the invention, the initiator absorbs photons to form a free radical which reacts with an allyl group of the photo-crosslinkable group. In various embodiments, the initiator can be an acetophenone derivative, camphorquinone, Irgacure® (1-hydroxy-cyclohexyl-phenyl-ketone, 1-[4-(2 -hydroxy-ethoxy)-phenyl]-2-hydroxy-2-methyl-1-propane-1-one, 2,2-dimethoxy-1,2-diphenylethan-1-one, or 2-methyl-1-[4-(methylthio)phenyl]-2-(4-morpho-linyl)-1-propanone),
Darocur® (1-[4-(2-hydroxyethoxy)-phenyl]-2-hydroxy-2-methyl-1-propane-1-one or 2,4,6-trimethylbenzoyl-diphenyl-phosphineoxide), and eosin dye.

The invention further provides a thermally crosslinked biodegradable/biocompatible elastomeric polymer, and a photo-crosslinked biodegradable/biocompatible elastomeric polymer.

According to a further aspect of the invention there is provided a method of preparing a thermally crosslinked biodegradable/biocompatible elastomeric polymer comprising: preparing a star co-polymer from at least one monomer and an initiator, said at least one monomer capable of forming a biodegradable linkage to another monomer and capable of undergoing ring-opening polymerization, combining the star co-polymer with a bis-lactone crosslinking agent, and heating the combined star co-polymer and crosslinking agent, so that a crosslinked biodegradable/biocompatible elastomeric polymer is prepared. In various embodiments, the said at least one monomer is selected from lactones, carbonates, and cyclic amides, and the initiator can be a polyol. In one embodiment, the bis-lactone crosslinking agent can be (2,2-)bis (ε-caprolactone-4-yl)propane (BCP).

In accordance with yet another aspect of the invention there is provided a method of preparing a photo-crosslinked biodegradable/biocompatible elastomeric polymer comprising: preparing a photo-crosslinkable star co-polymer from at least one monomer capable of forming a biodegradable linkage to another monomer and capable of undergoing ring-opening polymerization, the star co-polymer further comprising one or more photo-crosslinkable groups on the polymer chain termini combining the photo-crosslinkable star co-polymer with an initiator, and exposing the combined star co-polymer and initiator to photo-crosslinking light; so that a crosslinked biodegradable/biocompatible elastomeric polymer is prepared.

According to a further aspect, the invention provides a device comprising a biodegradable/biocompatible elastomeric polymer. In some embodiments the device is a biomedical device selected from a needle, stent, and catheter. In other embodiments the invention provides a coating material on a metallic biomedical device such as a needle, stent, or catheter. In a further embodiment, the device is a scaffold for tissue engineering.

In yet another aspect of the invention, there is provided an implantable drug delivery device comprising a biodegradable/biocompatible elastomeric polymer and a pharmaceutical agent.

BRIEF DESCRIPTION OF THE DRAWINGS

Embodiments of the invention will now be described, by way of example, with reference to the accompanying drawings, wherein.

DETAILED DESCRIPTION OF THE INVENTION

Figure 1:
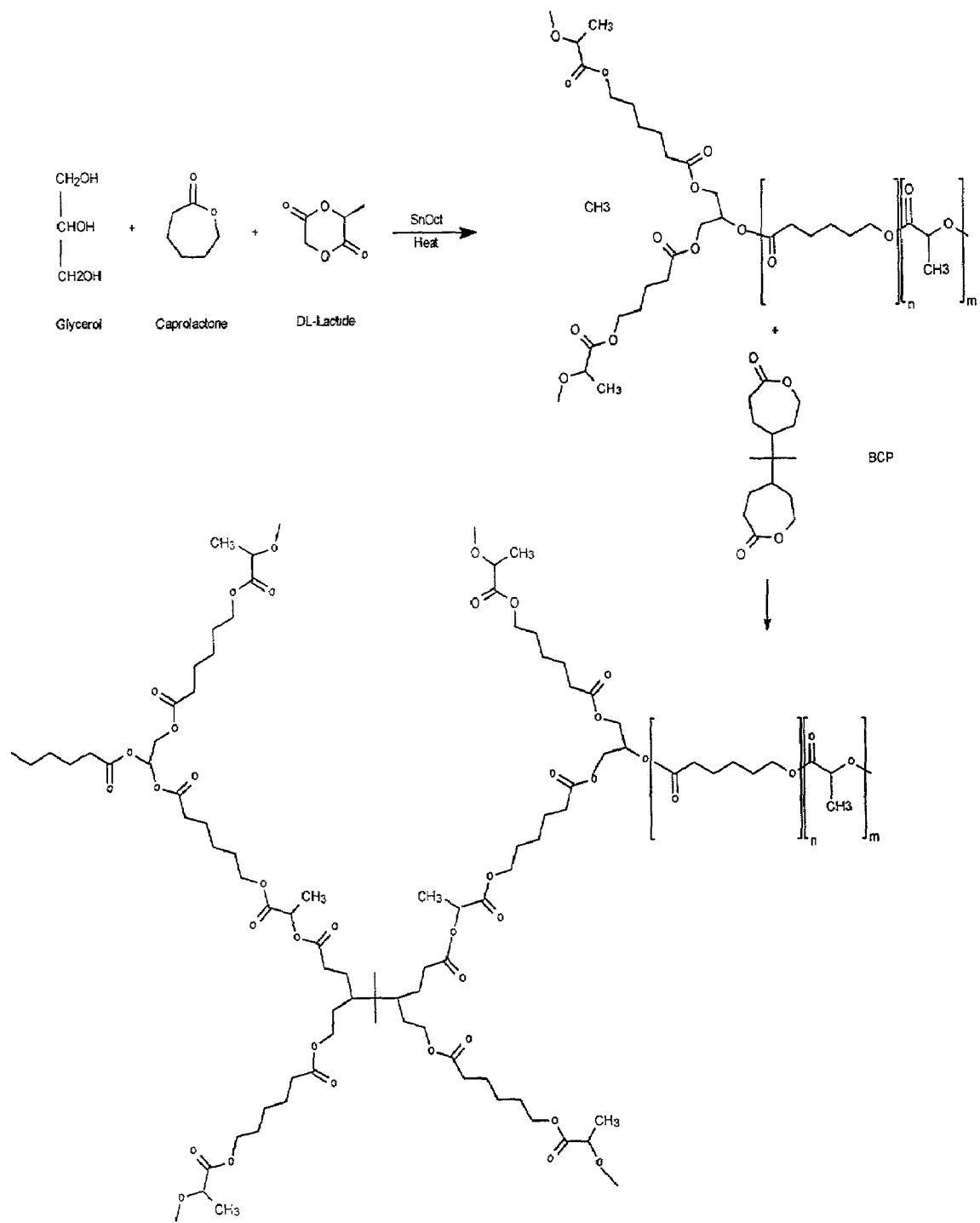
FIG. 1 shows the preparation of a thermoset elastomeric polymer using BCP ((2,2-)bis(ε-caprolactone-4-yl)propane) according to an embodiment of the invention.

In accordance with a broad aspect, the present invention provides biodegradable and/or biocompatible elastomeric polymers. The elastomeric polymers of the invention can be thermally or photically crosslinked. These elastomers are useful in applications such as, for example, biomaterials and biomedical devices, where they can be used in treatment of human and non-human subjects, and in applications such as tissue engineering. Elastomers of the invention can be formed into films, rods, screws, needles, stents, catheters, or other structures with or without incorporated fibres; implantable drug delivery systems, in which a pharmaceutical agent is disposed in the elastomer; film coatings for pills; scaffolds for tissue engineering of soft tissues in vitro and in vivo coatings on biomedical devices such as needles, stents, and catheters; as well as other applications such as rubber tougheners for ceramic devices.

Other applications of the elastomers of the invention include applications where delivery of an agent encapsulated in, or loaded into, a biodegradable/biocompatible polymer is required, or would be beneficial. For example, in agriculture, an elastomer of the invention can be loaded with one or more agents such as a fertilizer or pesticide. Application of the loaded elastomer to a crop results in sustained-delivery of the one or more agents. Such delivery helps to avoid over-fertilizing of crops, and reduces or eliminates the need for repeated applications of such agents. Depending on the properties of the agent loaded into the elastomer, and the desired delivery rate of the agent, an excipient, as described below, can be used together with such agent.

As used herein, the term "biodegradable" is intended to denote a substance that can be chemically degraded, for example, via hydrolysis, or decomposed by natural effectors, for example, via weather or biological processes, such as enzyme activity. Such biological processes can take place within an organism or outside of an organism.

As used herein, the term "biocompatible" is intended to denote a substance having substantially no known toxicity to or adverse affects on biological processes. The substance can be a compound in its original state or one or more components of compound as the compound biodegrades.

Accordingly to one aspect of the invention there is provided a thermally crosslinked biodegradable/biocompatible elastomeric polymer. The elastomeric polymer is prepared by reacting a star co-polymer with a bis-lactone crosslinking agent at an elevated temperature. The inventors have discovered that bis-lactones can be used as crosslinking agents with star polymers that are living polymers in the preparation of biodegradable/biocompatible elastomers. This crosslinking strategy has not been demonstrated to date.

Suitable star co-polymers can be prepared from any monomer capable of forming a biodegradable linkage to another monomer and capable of undergoing polymerization through a condensation reaction, or preferably through a ring-opening reaction. Such monomers include, for example, any lactone, any carbonate, or any cyclic amide (e.g., polyester amides, polyamides), and any combination thereof can be used to prepare a star co-polymer in accordance with the invention. Examples of such monomers are valeroiactone, caprolactone, dioxepanone, lactide, glycolide, trimethylene carbonate, and O-benzyl-L-serine.

Requirements for the formation of a useful elastomer using a star co-polymer as a prepolymer are that the prepolymer has a glass transition temperature ($T_g$) below physiological temperature (e.g., 37° C.), and preferably below room temperature, and is amorphous. Glass transition temperature is the temperature at which a polymer undergoes a phase transition from a glassy state to a rubbey state upon heating. It is the temperature where the molecules of a polymeric solid begin to move relative to one another, yielding a substance that behaves like a rubber, rather than a brittle glass.

Thus, star co-polymers in which at least one monomer has a very low glass transition temperature are the most suitable. An example of a monomer suitable for use in accordance with the invention is ε-caprolactone ($T_g$=−60° C.). Such monomer can be used to prepare a star polymer, such as star co-polymer, with another monomer such as D,L-lactide, even though the glass transition temperature of D,L-lactide is 68° C.

In preparing a star co-polymer from one or more species of monomers, an initiator is used. The initiator can be any polyol, such as, for example, glycerol, pentaerythritol, and xylitol.

As noted above, a star polymer in accordance with the invention can comprise one or more species monomer. In general, the properties (e.g., physical properties such as strength, Young's modulus, etc., and degradation kinetics) of the elastomer are determined to a large extent by the composition of the star polymer, and, where two or more monomers are employed, by the molar ratios of the monomers. The elastomeric properties of the elastomer can also be varied by varying the amount of crosslinking agent employed, relative to the amount of star polymer. For example, where an elastomer having more rapid biodegradation kinetics is desired, a monomer that either biodegrades more rapidly, and/or is more hydrophylic, should be chosen for incorporation into the star co-polymer. Similarly, where an elastomer having greater elasticity is desired, the amount of crosslinking agent can be reduced. Thus, in the above example of a co-polymer of ε-caprolactone and D,L-lactide, polymers can be prepared with molar ratios ranging from 100:0 to 0:100, respectively. However, increasing the D,L-lactide content increases the biodegradation rate of the elastomer. It will be appreciated that, in accordance with the invention, an elastomer having a desired set of physical properties, including biodegradation rate, can be prepared by designing a star polymer with a specific architecture, and controlling the amount of crosslinking agent used. Moreover, such an elastomer is easily reproduced.

In accordance with another aspect of the invention, there is provided a photo-crosslinked biodegradable/biocompatible elastomeric polymer. In this aspect, a star co-polymer as described above is modified such that it contains one or more photo-crosslinkable groups on the polymer chain termini. A suitable photo-crosslinkable group is any group with an accessible carbon-carbon double bond that can undergo free radical polymerization. Examples of photo-crosslinkable groups are acrylate, coumarin, thymine, cinnamates, diacrylates, oligoacrylates, methacrylates, dimethacrylates, and oligomethacrylates. The photo-crosslinking reaction is initiated by a compound which absorbs photons to form a free radical which reacts with the allyl group of the photo-crosslinkable group. Examples of such an initiator are acetophenone derivatives (2,2-dimethyl-2-phenylacetaphenone, 2-methoxy-2-phenylacetaphenone), camphorquinone, Irgacure® (1-hydroxy-cyclohexyl-phenyl-ketone, 1-[4-(2-hydroxyethoxy)-phenyl]-2-hydroxy-2-methyl-1-propane-1-one, 2,2-dimethoxy-1,2-diphenylethan-1-one, or 2-methyl-1-[4-(methylthio)phenyl]-2-(4-morpho-linyl)-1-propanone), Darocur® (1-[4-(2hydroxyethoxy)-phenyl]-2-hydroxy-2-methyl-1-propane-1-one or 2,4,6-trimethylbenzoyl-diphenyl-phosphineoxide), and eosin dye. The wavelength (e.g., visible, ultraviolet (UV)) and intensity of light used for the photo-crosslinking reaction depend on the specific initiator used.

An advantage of photo-crosslinking is that a biodegradable elastomer can be prepared at room or physiologic temperature in vitro or in vivo. The photo-crosslinking reaction is rapid which makes it particularly suitable for the manufacture of drug-loaded polymer implants.

Among the many advantages of the elastomeric polymer of the invention are:
1. The prepolymer is a star co-polymer which has a reduced viscosity when in melt form which allows for easier insertion into molds for part manufacture, thus they can be processed at lower temperatures than their linear counterparts.
2. The prepolymer is amorphous (non-crystalline) and produces an amorphous elastomer which degrades at a more homogeneous rate than would a thermoplastic elastomer which relies on crystalline blocks of homopolymer sections of the backbone to provide crosslinks (amorphous regions degrade first, then the crystalline regions which degrade much slower).
3. Because of its homogeneous degradation rate, the elastomer maintains its physical properties for a longer time period (provides a linear decrease in strength with respect to mass loss during degradation).
4. The elastomer is biodegradable and biocompatible.

In accordance with another aspect of the invention, there is provided a drug delivery device, As noted above, the biodegradable and biocompatible photo-crosslinked elastomers of the invention are particularly well suited for drug delivery devices, such as controlled release devices. Firstly, an elastomer device surgically implanted in a subject provides administration of a drug at a desired location, with sustained slow release and depot effect, so that the total dosage administered to a subject can be reduced, and the potential for systemic side effects is reduced. Secondly, because the elastomer is biodegradable and biocompatible, the need for further surgery to retrieve the delivery device is avoided. Thirdly, the elastomer device may protect the drug from degradation until it is released. Lipophilic drugs, (for example, but not limited to bupivacaine, benzocaine, lidocaine, camptothecin, paclitaxel, etoposide, vincristine, vinblastine, vitamin D, tacrolimus, hydrocortisone, nitroglycerin, fentanyl, estradiol, testosterone, cortisone and other corticosteroids), hydrophilic drugs (for example, but not limited to pilocarpine nitrate, aspirin, ibuprofen, potassium choride, ascorbic acid), and peptide and protein drugs (e.g., cytokines such as interferons, interleukins, granulocyte macrophage colony stimulating factor, and insulin, erythropoeitin, human growth hormone, epidermal growth factor, vascular endothelial growth factor, basic fibroblast growth factor), and combinations thereof, can be loaded into a delivery device using an elastomer of the invention.

In some embodiments an excipient is included in addition to a drug or drugs. Excipients, also referred to as bulking agents or osmotagens, are physiologically inert, and enhance delivery or increase the rate of delivery of a drug by generating osmotic pressure within the elastomer. The mechanism of osmotically controlled release is as follows: Upon immersion into an aqueous medium, drug release begins as water vapor penetrates the polymer matrix until it reaches a polymer encapsulated particle, hereafter referred to as a capsule. The water phase-separates and dissolves the solid drug at the polymer/drug interface, forming a saturated solution of drug and excipient particles. Under the reduced water activity gradient, water is drawn into the capsule, causing it to swell. If the osmotic pressure is great enough the polymer capsule wall ruptures. Due to the relaxation process of the elastomer, the capsule wall slowly collapses and the solution of drug and excipient particles is forced out through the rupture formed. This rupture and collapse process results in the drug being released at an almost constant rate. Osmotic drug delivery from monolithic polymer devices has been described (Michaels at al., U.S. Pat. No. 4,117,256; Di Colo, *Biomaterials.* 13(12):850–856, 1992; Amsden et al., *J. Controlled Rel.* 30:45–56, 1994) in non-biodegradable polymers such as poly(ethylene-vinylacetate) and silicone.

Various means of achieving localized delivery of protein drugs have been investigated and include the use of liposomes, polymer gels, and biodegradable microspheres. Problems with these prior delivery systems include relatively short drug release durations, inefficient drug loadings, insustained and/or incontrollable release rates, and inability to maintain protein stability. Such delivery systems may subject proteins to conditions leading to aggregation, denaturation and adsorption at interfaces, deamidation, isomerization, cleavage, oxidation, thiol disulfide exchange, and β elimination in aqueous solutions. The major factors affecting these changes are mechanical forces such as shear, the presence of surfactants, buffers, ionic strength, the presence of oxidizers such as ions, radicals and peroxide, light, pH, temperature, and material surface interactions. Protein denaturation may result in a loss of potency and the conformation changes in the protein molecule may make the protein immunogenic.

The invention is particularly advantageous where peptide and protein drugs are used, which drugs are sensitive to environmental conditions as discussed above. A protein delivery device of the invention overcomes such problems by providing a polymeric delivery system capable of long-term, relatively constant protein delivery from a biodegradable and biocompatible elastomer device. The elastomer minimizes or avoids acidic degradation of a protein incorporated therein, because the elastomer and its degradation products are not acidic and are biocompatible. That is, the poly(caprolactone) homopolymer used in the elastomer of the invention degrades slower and produces fewer acidic degradation products per molecular weight than do other biodegradable polymers, such as poly(lactide-co-glycolide). These properties provide a more suitable pH environment for protein stability within the polymer. Thus, the protein released is more likely to be bioactive and non-immunogenic. Continuous release from the elastomer is achieved by employing an osmotic mechanism and a balance of polymer physical properties with polymer degradation. Aggregation of the protein within the delivery device is minimized or avoided by incorporating the protein as a solid lyophilized with appropriate agents. The lyophilization agents also serve as a driving force for an osmotic drug delivery mechanism. Use of the photo-crosslinked elastomer of the invention allows the device to be fabricated at, e.g., room temperature, thereby avoiding heat which can denature a protein.

The principle of osmotic drug delivery has previously been demonstrated in a delivery system capable of delivering a variety of proteins at the same, almost constant release rate (Amsden et al., *J. Control. Rel.* 33:99–105, 1995). The proteins were released at the same rate because the driving force for release was the same in each case: the osmotic pressure generated by an inorganic salt. However, use of such salt should preferably be avoided because of its destabilizing effect on a protein and the potential for tissue irritation. The necessary polymer properties for this release mechanism are a radial extension ratio of greater than 1.05, a water permeation coefficient of between $10^{-9}$ and $10^{-12}$ g cm/cm$^2$ sec cm Hg, a degradation time of greater than 1 month, and minor tissue irritation and inflammation upon implantation. In the previous work, non-degradable polymers such as silicone and poly(ethylene-co-vinyl acetate) were used. With such polymers a device geometry having a constant cross-sectional area is required in order to provide a constant release rate, because the osmotic rupturing mechanism proceeds in a serial manner from the surface to the interior of the device. As one moves from the exterior of the device, usually cylindrical in shape, to the interior, fewer and fewer drug capsules exist within each rupturing layer. This reduction in the number of capsules produces a declining release rate with time.

However, this problem is overcome by the biodegradable elastomers of the invention. Due to their biodegradable nature, their mechanical properties change with time. This property produces a drug-loaded device exhibiting a constant release rate. Although the mass of drug per cross-sectional area of the device is difficult to manipulate, the time required to produce a rupture of the elastomer is more easily manipulated. This latter parameter is determined by the extension ratio and Young's modulus of the polymer. Thus, according to the invention, the elastomer can be tailored such that its Young's modulus decreases with time while the extension ratio remains essentially constant during the release period without significant polymer degradation, such that the time required to rupture the polymer decreases with time. So long as this decrease keeps pace with the decrease in the mass of drug per cross-sectional area of the device, a constant release rate is achieved.

In one embodiment, an osmotic excipient is used in the protein delivery device. The excipient reduces protein aggregation and enhances osmotic protein delivery. Examples of suitable excipients include, but are not limited to, polyols (e.g., trehalose, polyethylene glycol, glycerin, mannitol) and small, neutral amino acids, and combinations thereof. Polyols are preferable because they can generate significant osmotic pressures and are highly effective at preventing protein aggregation. They accomplish this by re-ordering the water around the protein molecule, exerting pressure to reduce the surface contact between the protein and the solvent. This pressure forces hydrophobic portions of the protein to become further removed from the solvent, thus decreasing the likelihood of a hydrophobic-hydrophobic interaction leading to aggregation. Thus, in accordance with the invention, the protein is combined with an excipient by, for example, lyophilization. The ratio of excipient to protein can range from 1:1 to 99:1, depending on the specific conditions. A suspension of the protein/excipient is added to the photo-crosslinkable polymer of the invention prior to crosslinking, and is contained with in the elastomer upon crosslinking.

All cited documents are incorporated herein by reference in their entirety.

The invention is further described in the following non-limiting Examples.

WORKING EXAMPLES

Example 1

Thermally Crosslinked Elastomer

A rubbery polymer was made by first preparing a star co-polymer composed of D,L-lactide and ε-caprolactone. This co-polymer was crosslinked using a synthesized difunctional bis-ε-caprolactone (see FIG. 1). The procedures for each process are outlined below.

Preparation of Poly(star-D,L Lactide-co-ε-capolactone) (SCP)

Pure D,L-lactide (DLL or DL) from PURAG was used as received, and ε-caprolactone (ε-CL or CL) from Lancaster was purified by distillation under reduced pressure in the presence of $CaH_2$. Glycerol and stannous octoate from Sigma were used as received.

Star co-polymers of varying total molecular weight and ε-caprolactone; D,L-lactide monomer ratios were prepared. The preparation conditions are outlined in Table 1. A typical procedure, in which a 50:50 ε-CL:DLL co-polymer is prepared, is given below.

To a flame dried 20 mL glass ampoule was added 6 g purified ε-caprolactone, 7.6 g D,L-lactide, and 0.48 g glycerol. This mixture was placed in an oven at 140° C. for 15 minutes after which time the D,L-lactide was melted. The resulting solution was mixed by vortexing and 1×10−4 mol stannous octoate/mol monomer was added. The solution was purged with nitrogen for 5 minutes and the ampoule then sealed under vacuum. The sealed ampoule was placed in the oven at 140° C. for at least 16 hours. The resulting polymer structure was confirmed using NMR. The glass transition temperature of the viscous polymer was determined to be −20° C. using a Seiko DSC and its weight-average molecular weight has been determined to be 2100 g/mol via GPC with a Precision Detectors combination static/dynamic light scattering detector.

TABLE 1

Preparation conditions of star co-polymers.

| ε-CL:DLL | ε-CL (g) | DLL (g) | Glycerol (g) | Mw | Appearance |
|---|---|---|---|---|---|
| 50:50 | 6 | 7.6 | 0.48 | 2700 | clear, viscous liquid |
| 70:30 | 8.8 | 4.8 | 0.48 | 2700 | clear liquid |
| 30:70 | 3.4 | 10.2 | 0.48 | 2700 | clear, very viscous liquid |
| 90:10 | 11.9 | 1.7 | 0.48 | 2700 | white solid |
| 10:90 | 1.1 | 12.5 | 0.48 | 2700 | clear solid |
| 50:50 | 12.2 | 15.4 | 0.48 | 5400 | clear, very viscous liquid |
| 50:50 | 18.4 | 23.3 | 0.48 | 8100 | clear, very viscous liquid |
| 50:50 | 37.1 | 46.9 | 0.48 | 16200 | clear, very viscous liquid |

Synthesis of Crossinking Agent: (2,2-)Bis(ε-caprolactone-4-yl)propane (BCP)

5.40 g of 2,2-bis(4-hydroxycyclohexyl)propane were dissolved in 29.5 mL glacial acetic acid. 5.50 g of CrO3 were dissolved in dilute acetic acid solution (25 mL of glacial acetic acid and 4.0 mL of distilled water). The $CrO_3$ solution was added drop by drop to the first solution over a period of about 2 hours during stirring and cooling at 17–18° C. using a circulating water bath. After 0.5 hours of the reaction, 25 mL of 2-propanol was added to the water-cooled solution. The solution was left to stand overnight. The solution was concentrated under reduced pressure in a fumehood. The remaining solution was poured into distilled water where powdery white crystals precipitated. The solution was filtered using Whatman No.1 filter paper and the cake washed several times with distilled water until white. The cake of white crystals was then dried under vacuum in the fumehood. This white powder was dissolved in benzene and filtered using Whatman No.1 filter paper. The filtrate was retained and evaporated to yield 4.1 g of white crystals of the 78% diketone (DSC m.p 163° C.).

The diketone was then dissolved in a sufficient quantity of dichloromethane to undergo a Bayer-Villiger oxidation to yield the BCP. The procedure was as follows: 3.9 g (0.259 mol) of m-chloroperoxybenzoic acid was added in batches to a stirred solution of diketone in dichloromethane $CH_2Cl_2$. (N.B. m-chloroperoxybenzoic was previously dried with $MgSO_4$ in dichloromethane prior to use. Both m-chloroperoxybenzoic and $MgSO_4$ were dissolved in a sufficient quantity of dichloromethane and then filtered. The filtrate was dried under vacuum in a fumehood to yield the dried m-chloroperoxybenzoic.) The product was purified by re-crystallization in 2-heptanone. Purified crystals were filtered and dried. A pure white crystalline powder was obtained which was characterized by DSC, H-NMR, $C^{13}$-NMR, IR, elemental analysis, and electron impact mass spectrometry. The final product had a molecular weight of 268 and a melting point of 210–215° C., The product yield was 65% and had a purity greater than 95%.

Thermal Curing to Yield Elastomer

To a flame dried 5 ml ampoule was added 0.5 g of BCP and 0.5 g ε-CL. The ampoule was purged with dry nitrogen and then placed in a vacuum oven at 180° C. for 10 minutes after which time the BCP was completely dissolved in the ε-CL monomer. A vacuum pressure of 20 mm Hg was applied for 5 minutes to draw out dissolved oxygen. To this solution was added 1 g of star co-polymer which had been pre-heated to 180° C. A drop ($10^{-4}$ mol) of stannous octoate was added, the solution was quickly mixed by vortexing and then sealed under vacuum and placed in the vacuum oven at 180° C. for at least 4 hours, It should be noted that varying amounts of BCP:star co-polymer can be added to achieve varying elastomeric properties. Physical properties of elastomers prepared in this way are given in Table 2.

TABLE 2

Physical Properties of Biodegradable Elastomers Prepared Using BCP

| SCP[a]:BCP (g) | $T_g$ (° C.) | Extension ratio, $\lambda_b$ | Young's modulus (MPa) | Ultimate tensile strength (MPa) |
|---|---|---|---|---|
| 3:0.75 | −21.0 | 3.8 | 0.13 | 0.27 |
| 3:1.00 | −18.1 | 3.3 | 0.22 | 0.33 |
| 3:1.25 | −14.0 | 2.1 | 0.33 | 0.37 |
| 3:1.50 | −11.3 | 2.0 | 0.51 | 0.67 |

[a]star co-polymer (50:50 ε-CL:DLL)

Example 2

Photo-Crosslinked Elastomer

Figure 2:
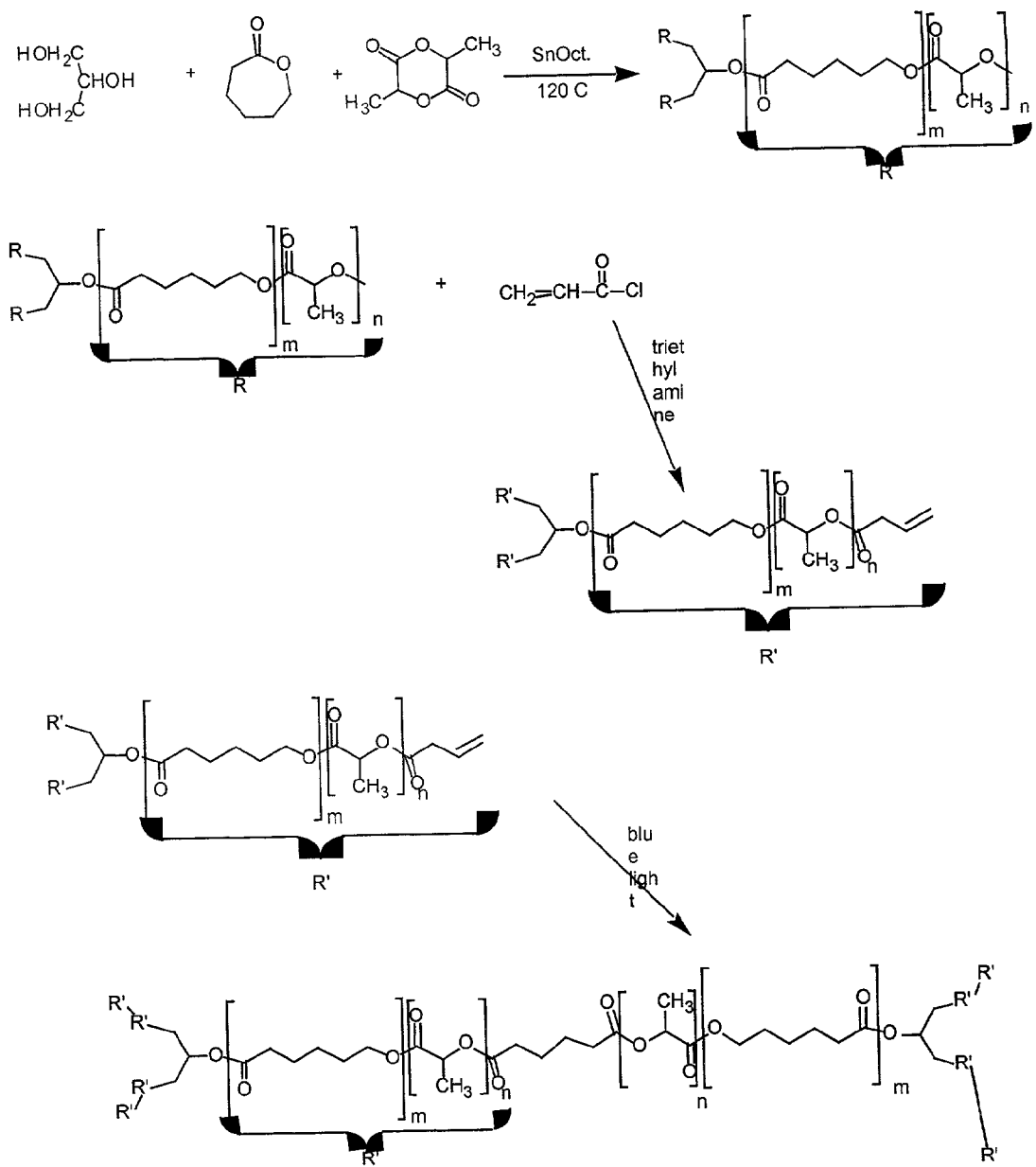
FIG. 2 shows the preparation of a photo-crosslinked elastomeric polymer according to an embodiment of the invention.

A reaction scheme for the following method of preparing an elastomer using a photo-crosslinkable polymer is shown in FIG. 2, and procedures are given below.

Preparation of Acrylate Terminated Star Co-polymer

In a round bottom flask, 10 g of SCP ($5 \times 10^{-3}$ mole) was dissolved in 100 ml of dichloromethane (DCM) using a magnetic stirrer. The flask was sealed using rubber septum and flushed with argon gas to remove the oxygen. This process was repeated every hour throughout the procedure. The flask was then immersed in an ice bath to drop the temperature of the solution to 0° C. After reaching 0° C., 1.25 ml of acryloyl chloride (ACLR) (0.015 mole), 2 ml of triethylamine (TEA), and 5 mg of dimethyl aminopyridine (DMAP) were added in a step wise manner over a period of 12 hours while the solution was kept at 0° C. The reaction was continued at room temperature for another 12 hours. The reaction completion was detected using TLC plates. The final solution was filtered to remove triethanolamine HCl salt, then evaporated using a rotary evaporator, and the residue was purified by precipitation in diethyl acetate. The solution was filtered and then ethyl acetate was evaporated. The final pure acrylated SCP was tested using Fourier Transform Infra-Red, 1H-NMR and $^{13}$C-NMR for the disappearance of OH groups and the formation of C=C bonds.

Using this method, the amount of ACLR has been varied so as to provide varying degrees of acrylation of the star co-polymer.

UV-crosslinking of Acrylated SCP 3 g of acetophenone (a UV initiator) was dissolved in 10 ml DCM to provide 30% w/v concentration of this solution. A 50% w/v solution of acrylated SCP in DCM (5 g in 10 ml) was prepared. On a watch glass, to every 1 ml of this acrylated SCP solution, 10 μl of the 30% acetophenone solution was added. The solution was exposed to UV light using a Black Ray UV100 AP lamp, 21,700 μW/cm² at 5 cm, for 30–60 seconds to crosslink. The UV crosslinking process was completely successful and resulted in the formation of an elastomer.

Argon Laser Crosslinking of Acrylated SCP 5 g of acrylated SCP was mixed with 7.1 mg (1 mM) of ethyl eosin, 0.3 g of triethanolamine (200 mM), and 10 μl of 1-vinyl-2-pyrrolidinone in 10 ml DCM. The solution was exposed to an argon laser at wavelength (λ) of 514 nm and a power range between 20–100 mW for several seconds. The laser crosslinking process was completely successful and resulted in the formation of an elastomer.

Results and Discussion

Figure 3:
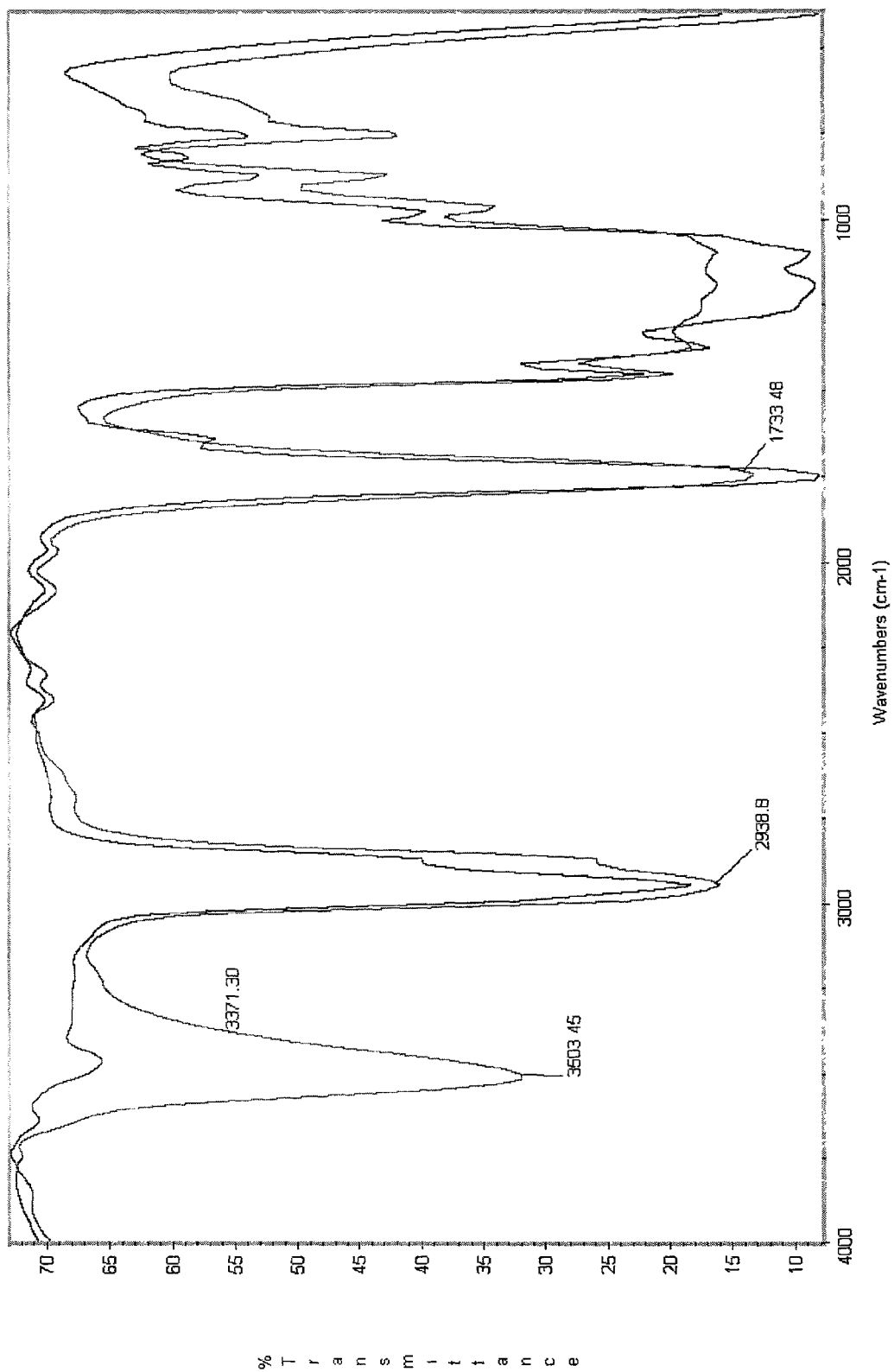
FIG. 3 shows the IR spectrum of SCP (star co-polymer) before and after reaction with acryloyl chloride.

FIG. 3 shows the IR spectrum of SCP before and after the reaction with acryloyl chloride. The SCP shows an OH stretching vibration at 3500 cm$^{-1}$, which totally disappeared once reacted with acryloyl chloride, This indicates that the OH functional group at the chain terminal of SCP was totally blocked through the formation of the conjugate system holding the C=C.

Figure 4:
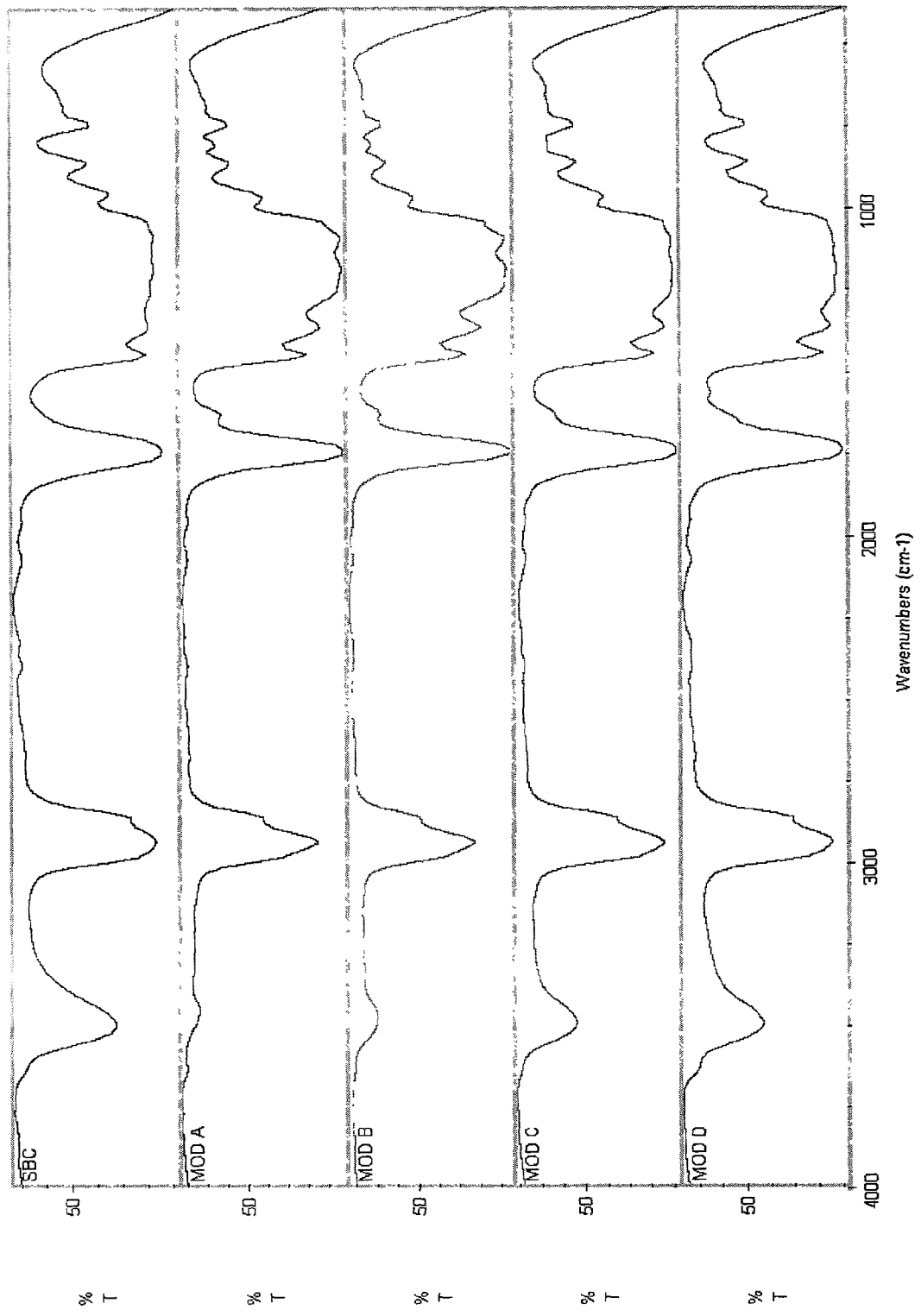
FIG. 4 is an IR spectrum of SCP showing a gradual increase in the intensity of OH stretching as the amount of acryloyl chloride used decreases (SCP: star co-polymer before reacting with acryloyl chloride; MOD A: 1 mole SCP reacted with 3.0 moles ACLR; MOD B: 1 mole SCP reacted with 2.4 moles ACLR; MOD C: 1 mole SCP reacted with 1.2 moles ACLR; MOD D: 1 mole SCP reacted with 0.5 moles AGLR)

The decrease in the intensity of this IR stretching depends on the amount of acryloyl chloride used to react with SCP. FIG. 4 shows the gradual increase in the intensity of the OH stretching as the amount of acryloyl chloride used decreases (less OH is converted to become C=C). This is considered a very important issue in controlling the crosslinking density. By manipulating the number of anchors (C=C in this case) that will participate in the UV/Laser crosslinking reaction, the elasticity and the strength of the cross-linked product can be manipulated.

Figure 5:
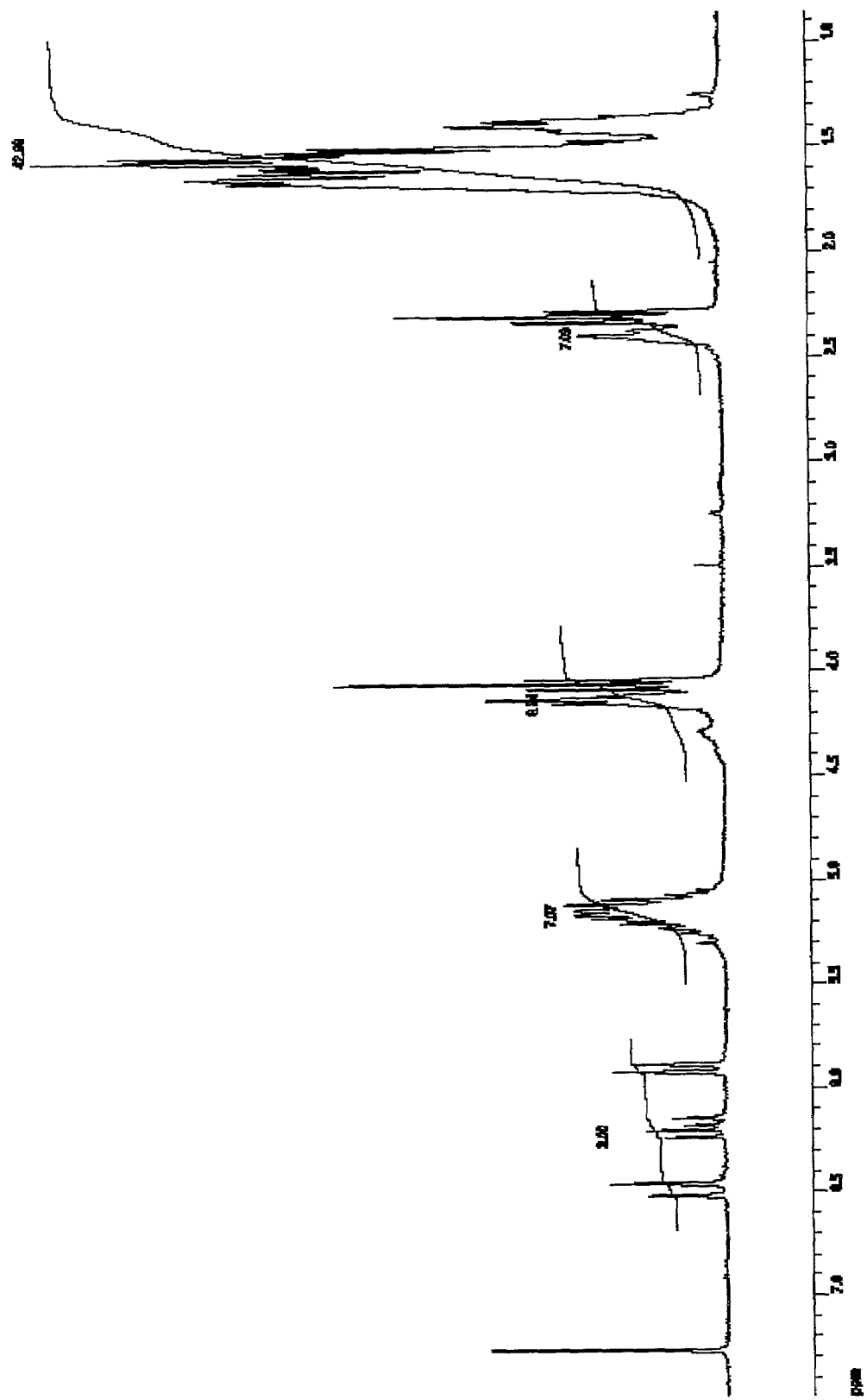
FIG. 5 shows a 1H-NMR spectrum of SCP before reacting with acryloyl chloride.

To confirm the formation of the C=C, both $^1$H-NMR and $^{13}$C-NMR were utilized, FIG. 5 shows the $^1$H-NMR spectrum of SCP before its reaction with acryloyl chloride. It is clear that no peaks are shown in the conjugated proton region between 5.5–7 ppm. On the other hand, two singlet (5.8 & 6.5 ppm) and one quartet (6.4 ppm) sharp peaks shown in FIG. 6 correspond to the protons of the conjugated system added to the chain through the reaction with acryloyl chloride.

Figure 6:
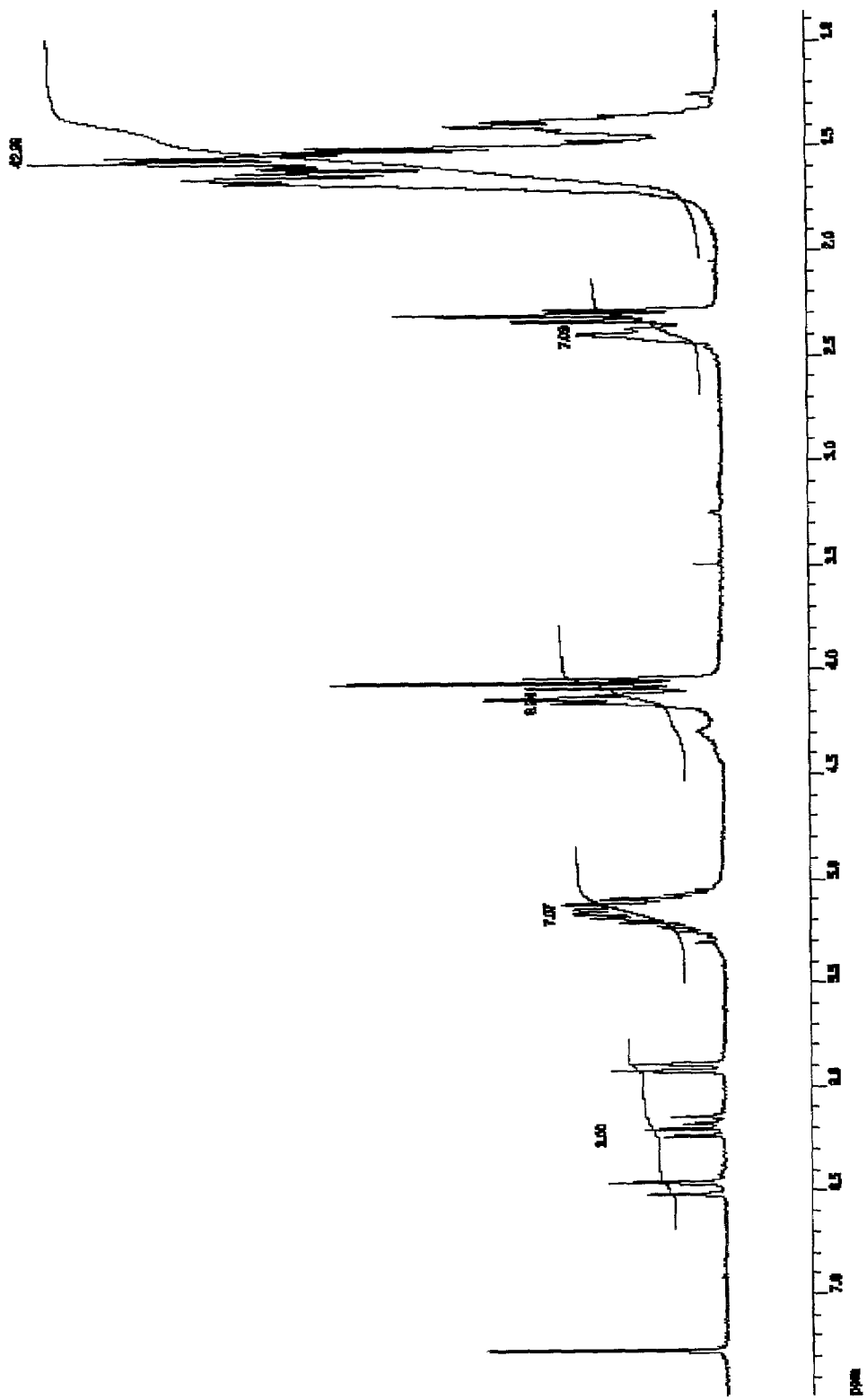
FIG. 6 shows a 1H-NMR spectrum of SCP after reacting with acryloyl chloride.
Figure 7:
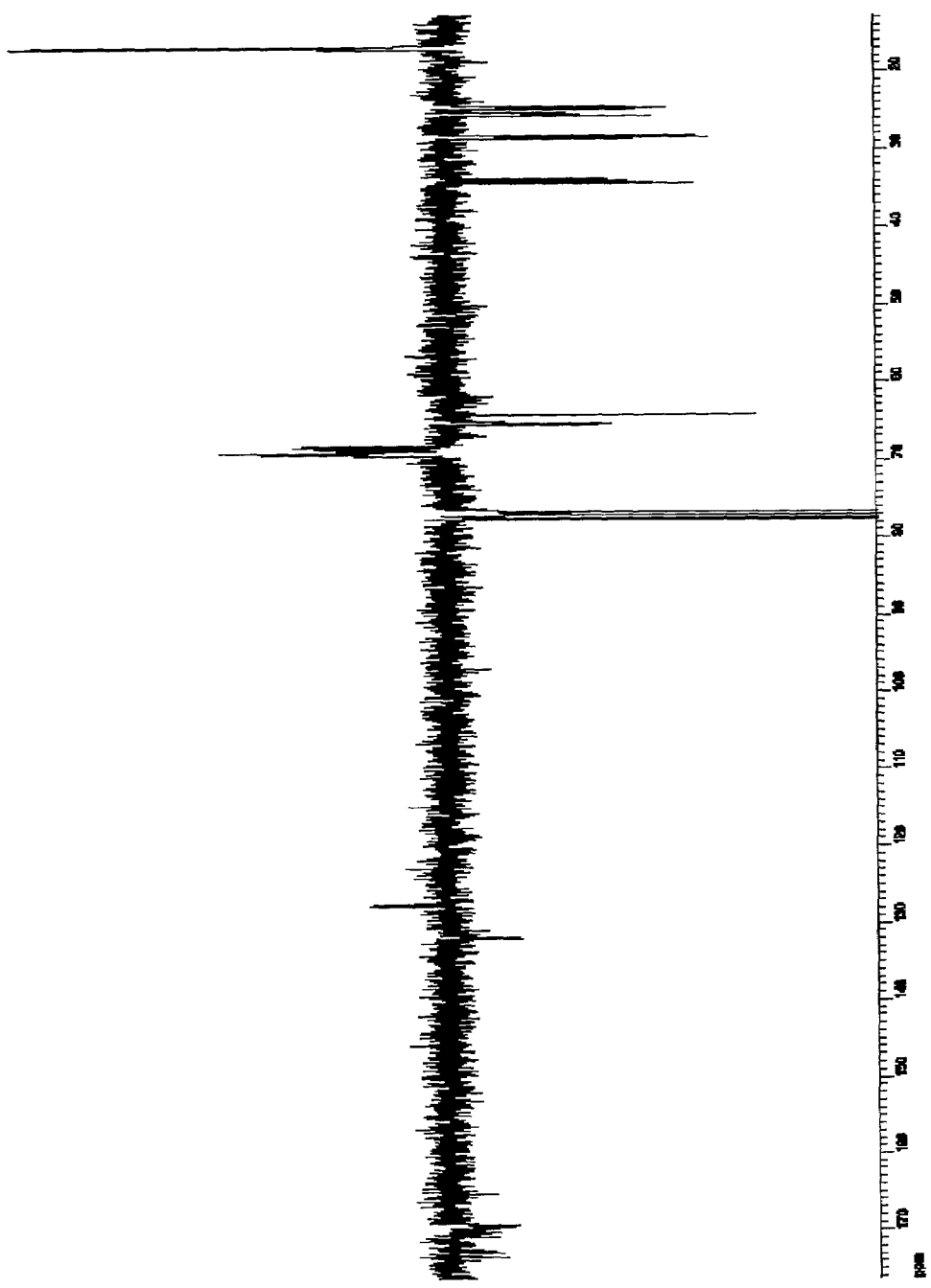
FIG. 7 shows a 13C-NMR spectrum of SCP reacted with acryloyl chloride.

Both FIGS. 6 and 7 confirm the purity of the final product through the absence of any interfering peaks, i.e., peaks not related to those expected or those which belong to the SCP protons and carbon backbone.

Example 3

Degradation of Elastomeric Polymer

Figure 8:
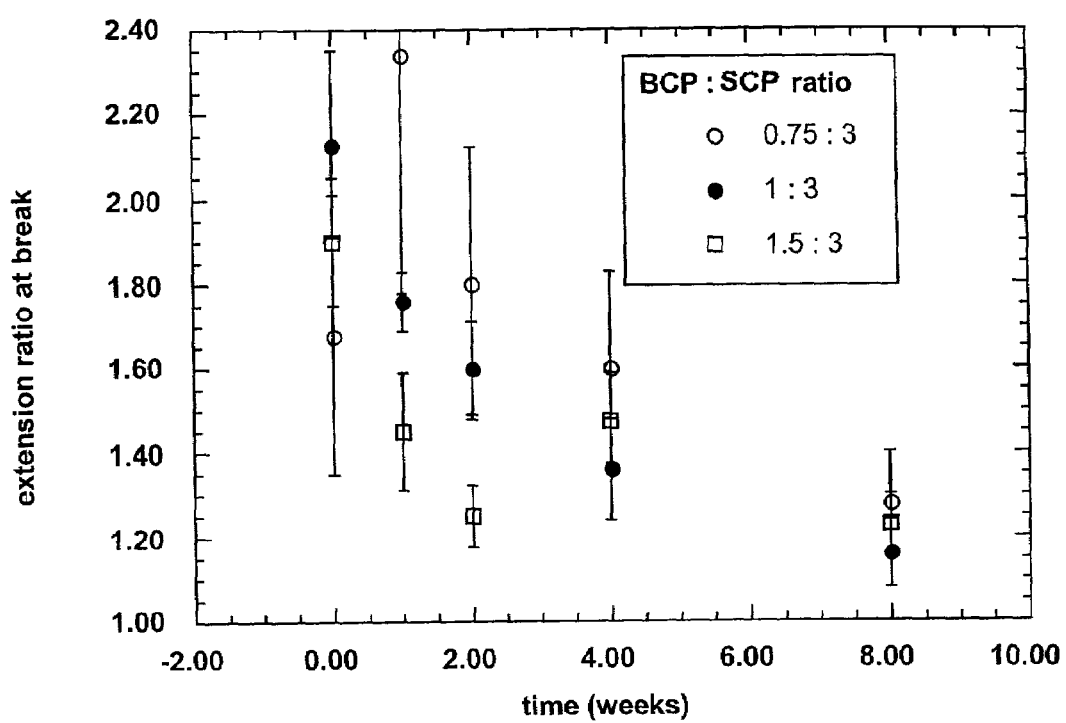
FIG. 8 shows the effect of degradation of the elastomer of Example 1 in PBS (pH 7.4) at 37° C. on extension ratio.
Figure 9:
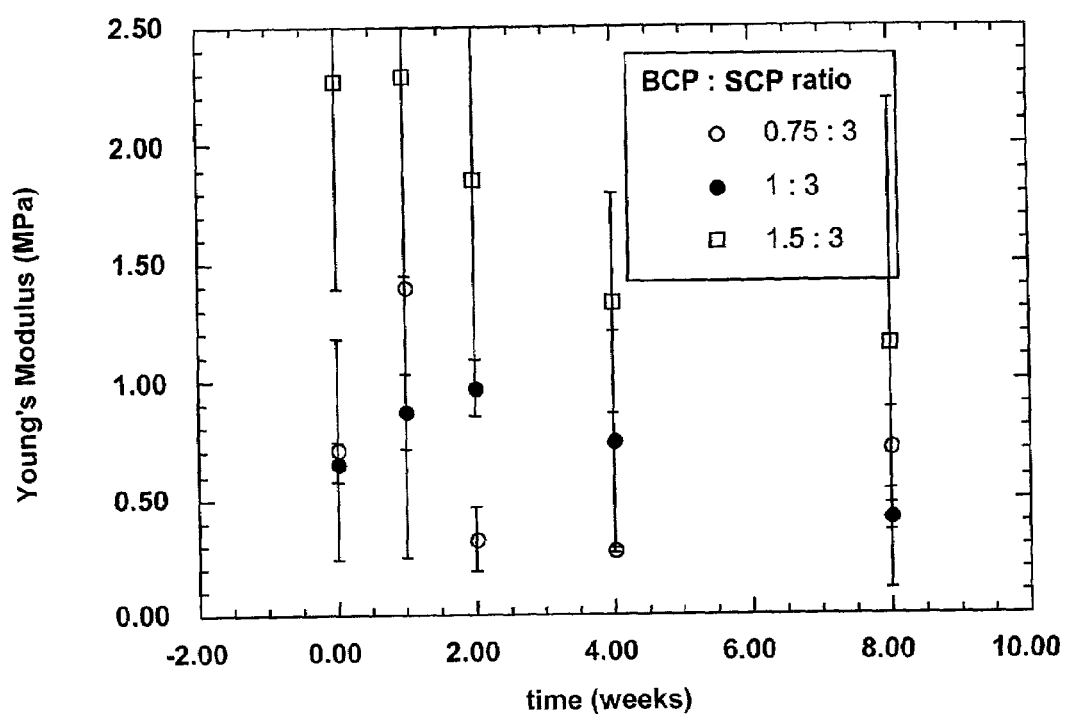
FIG. 9 shows the effect of degradation of the elastomer of Example 1 in PBS (pH 7.4) at 37° C. on Young's Modulus.
Figure 10:
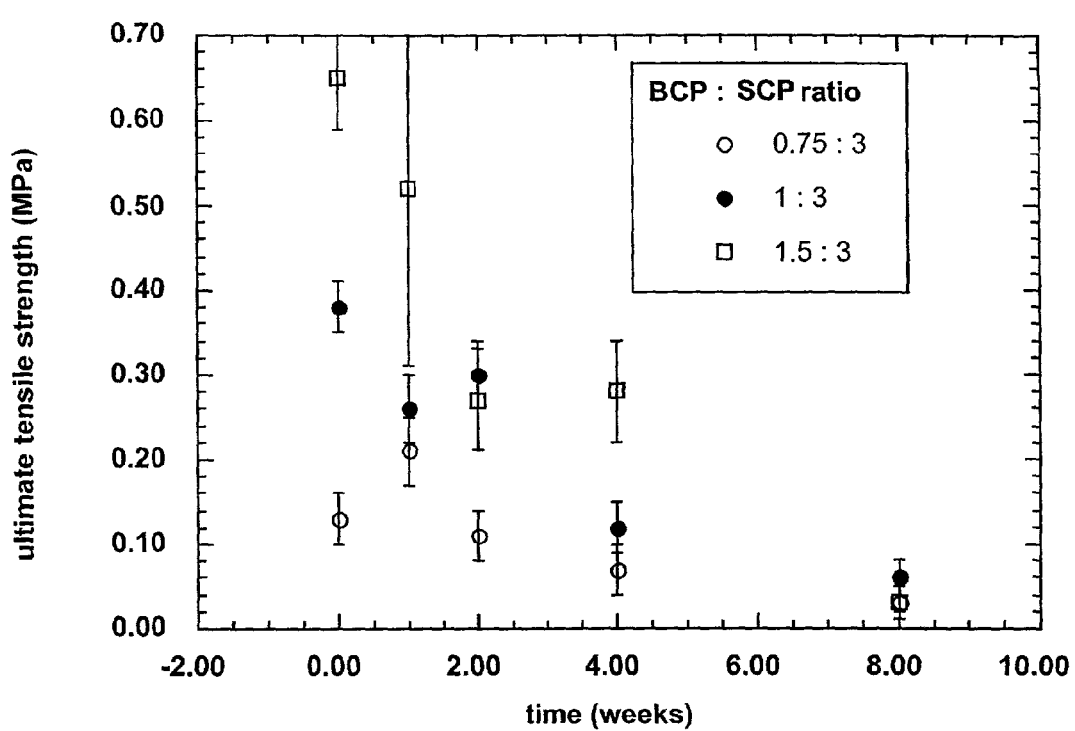
FIG. 10 shows the effect of degradation of the elastomer of Example 1 in PBS (pH 7.4) at 37° C. on ultimate tensile strength.

The thermoset elastomeric polymers described in Example 1 were tested for in vitro degradation rates in pH 7.4 phosphate buffered saline under gentle agitation. Results are shown in Table 3 and FIGS. 8 to 10.

Tensile properties (extension ratio. Young's Modulus, and ultimate tensile strength) of the elastomer were measured over an eight week period of degradation. Tensile properties were obtained at each time point of FIGS. 8 to 10 using an Instron model 4443 tensile tester (Instron Corporation, Canton, Mass.) equipped with an elastomeric extensometer, and using a crosshead speed of 50 cm/minute, as per ASTM 412. Each sample was pre-fabricated into strips about 7.5 cm×6 mm×3 mm. Each data point in the figures represents the average of from 3 to 5 samples and the error bars represent standard deviation.

Table 3 shows the mean percentage increase in weight of these elastomers over a twelve week period.

TABLE 3

Mean percentage Increase in weight of elastomers over a 12 week period.

| Ratio | Week 1 | Week 2 | Week 4 | Week 8 | Week 12 |
|---|---|---|---|---|---|
| 3:0.75 | 7.97 | 13.44 | 20.72 | 79.81 | — |
| 3:1.00 | 5.97 | 6.10 | 6.68 | 18.86 | 64.19 |
| 3:1.25 | 3.19 | 3.53 | 3.95 | 4.42 | 7.09 |
| 3:1.50 | 2.93 | 3.13 | 3.48 | 3.72 | 6.33 |

Example 4

Physical Properties of UV Crosslinked Elastomers Having Different Molecular Weight SCPs Method SCPs were prepared using the general method described in Example 2, but particulars of the procedure were substituted as indicated below, to arrive at the following SCPs of different molecular weights:

SCP1: A 50:50 molar ratio of ε-caprolactone and D,L-lactide with 0.017 moles of glycerol and $1 \times 10^{-4}$ mole of SnOct/mole of the monomer. This was prepared from 8.55 g of ε-caprolactone +10.8 g D,L-lactide+0.23 g glycerol+1 drop SnOct (140° C. 18 h).

SCP5: A 50:50 molar ratio of ε-caprolactone and D,L-lactide with 0.034 moles of glycerol and $1 \times 10^{-4}$ mole of SnOct/mole of the monomer. This was prepared from 8.55 g of ε-caprolactone +10.8 g D,L-lactide+0.46 g glycerol+1 drop SnOct (140° C. 18 h).

SCP6: A 50:50 molar ratio of caprolactone and D,L-lactide with 0.011 moles of glycerol and 1×10$^{-4}$ mole of SnOct/mole of the monomer. This was prepared from 8.55 g of ε-caprolactone +10.8 g D,L-lactide+0.15 g glycerol+1 drop SnOct (140° C. 18 h).

Each of these samples was reacted with acryloyl chloride and TEA according to the scheme set forth in Table 4.

TABLE 4

Details of reactions of SCPs with acryloyl chloride and TEA.

| Sample | Calculated MW | Amount Reacted (g) | Acryloyl Chloride (ml) | Triethyl-amine (ml) | DCM (ml) |
|---|---|---|---|---|---|
| SCP1 | 7829 | 20 | 0.6 | 1.1 | 200 |
| SCP5 | 3960 | 20 | 1.2 | 2.1 | 200 |
| SCP6 | 11960 | 20 | 0.4 | 0.68 | 200 |

For UV cross-linking, 1 gram of each of the three polymers was dissolved in 1 ml DCM. 50 μl of 30% w/v DMPA was then added to the solution. The solution was mixed using a vortex and then poured into Teflon® moulds (3 mm×3 mm×10 cm long). The samples were exposed to UV light (see Example 2) at a distance of 4 inches for 5 minutes.

An additional SCP was prepared as follows, but was not subjected to the tensile tests described below:

SCP2: A 70:30 molar ratio of ε-caprolactone and D,L-lactide with 0.05 moles of glycerol and 1×10$^{-4}$ mole of SnOct/mole of the monomer. This was prepared from 11.97 g of ε-caprolactone +6.48 g D,L-lactide+0.69 g glycerol+1 drop SnOct (140° C. 18 h), and yielded a clear, transparent, viscous semisolid.

For acrylation, 20 g of SCP2 was dissolved in 200 ml of DCM and reacted with 2.5 ml of acryloyl chloride and 4 ml TEA for 12 h at 0° C. and another 12 h at room temperature. The reaction was stopped by adding 2 ml ethanol. The solution was then filtered and evaporated to recover the semisolid non-pure acrylated polymer, which was then purified with ethyl acetate and left to dry overnight. Purity of the polymer was confirmed with TLC, IR, and NMR.

For UV crosslinking, 1 g of SCP2 was dissolved in 2 ml DCM, and 40 μl of 30% w/v 2,2-dimethyl -2-phenylac-etaphenone was added to the solution. The solution was vortex-mixed and then exposed to nitrogen to evaporate the DCM. The solution was then poured into Teflon moulds and exposed to UV light (see Example 2 for details) at a distance of 4 inches for 5 minutes.

Results

All SCPs were clear transparent masses that were different in viscosity, such that SCP6>SCP1>SCP5. After reaction with acryloyl chloride and TEA, appearance of the SCPs was as follows:

SCP1: Yellowish (+) in colour, transparent
SCP5: Yellowish (++) in colour, transparent
SCP6: Yellowish (+) in colour, transparent
SCP2: Yellowish (++) in colour, transparent In all four samples, TLC resulted in one spot of product, indicating that the compounds were relatively pure. IR indicated the disappearance of OH stretching vibrations at 3500 cm$^{-1}$ and the disappearance of any interfering peaks. NMR (not shown) confirmed the formation of C=C and the purity of the compounds.

UV-linking of the SCPs produced elastic polymers. All three samples exhibited elasticity, although SCP5 was tougher and more brittle than SCP1, and SCP6 was weaker and softer than SCP1. This result was expected since the co-polymer of SCP1 has shorter arms (more glycerol was used) compared to SCP6, which has longer arms resulting from using less of the initiator. SCPs was more elastic than SCP1. From among SCP1, SCP5, and SCP6, it was concluded that SCP1 and SCP6 were the best samples prepared and represent two different categories of UV elastomers, In terms of tensile strength.

Figure 11A:
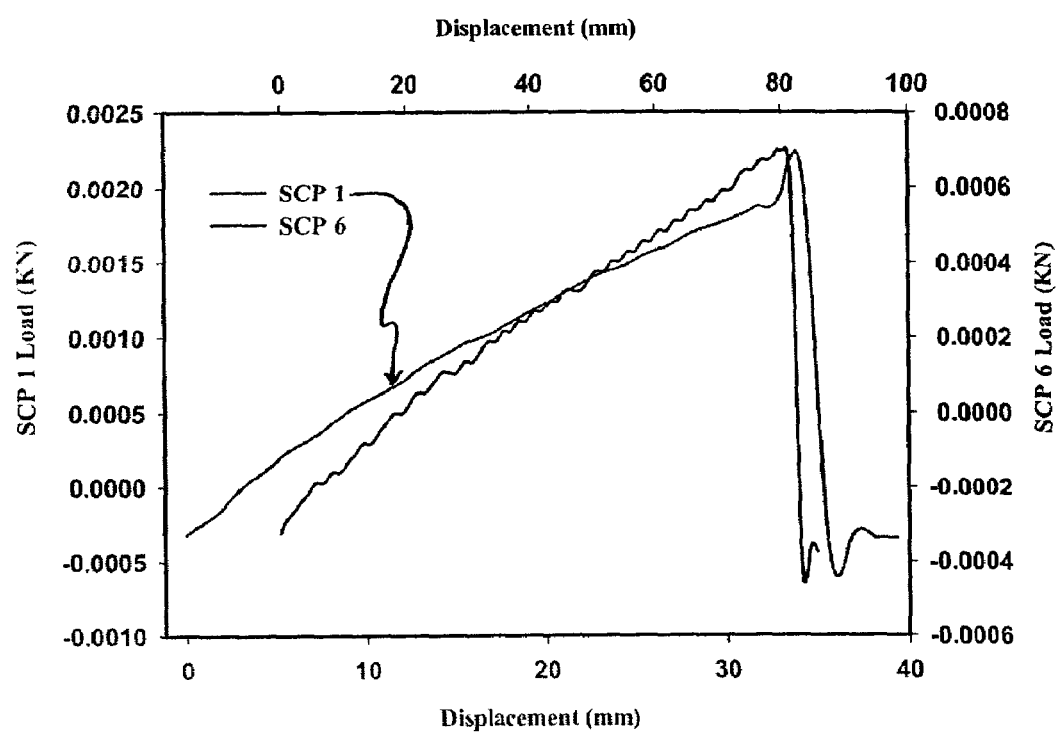
FIGS. 11A and 11B show results of tensile tests (strength, FIG. 11A; Young's modulus, FIG. 11B) of UV crosslinked polymers SCP1 and SCP6. Note the different scale for each sample. Each point represents the average of 4 measurements.
Figure 11B:
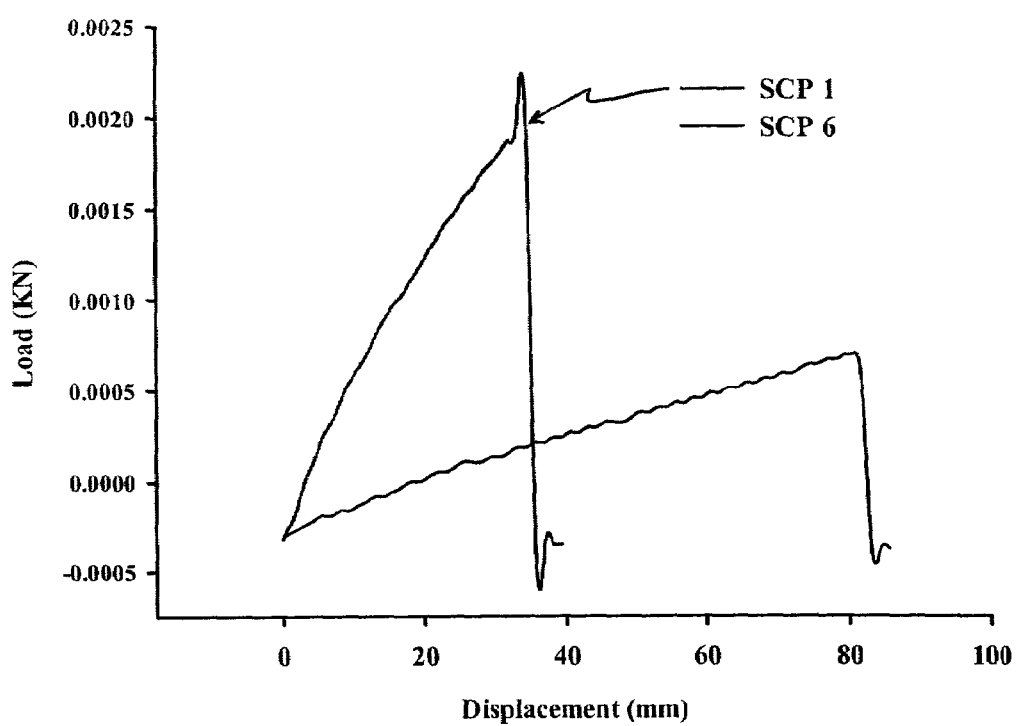

The tensile strength of SCP1 and SCP6 was measured using an Instron model 4443 universal tensile testing machine with a crosshead speed of 500 mm/min. Four specimens were used for each measurement. The results from the tensile strength tests confirmed that SCP1 had greater tensile strength than SCP6 (FIG. 11A). In FIG. 11B, it can be seen from the difference in slope (i.e., difference in Young's modulus) of the curves for SCP1 and SCP6 that SCP1 was less elastic than SCP6. It is expected that further manipulation of the star co-polymers and the monomer compositions (i.e., molar ratios) will produce changes in the physical properties of the elastomer similar to those changes reported in Example 5 for the thermally crosslinked elastomer.

Example 5

Manipulation of Physical Properties of Thermally Crosslinked Elastomer

Physical properties of the BCP crosslinked elastomer were manipulated by preparing star-co-polymers of different molecular weights (900, 1350, 1800 and 2700 g/mol per arm) and monomer compositions (i.e., molar ratios of 30:70, 50:50, 70:30, and 90:10 D,L-lactide:ε-caprolactone). Syntheses were carried out as described in Example 1.

(A) Characterization of Star-co-polymer Prepolymers

50:50 star-co-polymers of different molecular weights were all clear in appearance. 50:50, 900 (i.e, 900 g/mol Mw per arm) was a viscous liquid, 50:50,1350 and 50:50, 1800 polymers were more viscous, whereas 50:50, 2700 was very glassy, like a solid. 30:70, 900 was a low viscosity liquid and slightly white in colour, and 70:30, 900 polymers were clear and more viscous. Further increasing D,L-lactide to 90:10, 900 produced a polymer that was nearly glass-like.

Influence of Molecular Weight on Glass Transition Temperature ($T_g$)

To study the effect of molecular weight on $T_g$, star-co-polymers of molecular weights 900, 1350, 1800 and 2700 g/mol per arm were characterized by DSC and differential DSC (DDSC), wherein $T_g$ was located as the peak in the slope of the DSC curve.

All prepolymers had $T_g$s below room temperature (−20° C., −14° C., −13° C., and −11° C. for the 900, 1350, 1800 and 2700 g/mol per arm prepolymers, respectively), and $T_g$ increased with molecular weight. This increase in $T_g$ can be explained by the movement of the polymer chain segment. The higher the molecular weight, the bulkier the segment of polymer and the more energy required to move it. Therefore, the glass transition of a heavier prepolymer will be at a higher temperature.

Influence of Monomer Composition on Glass Transition Temperature

The effect of D,L-lactide to ε-caprolactone molar ratio on $T_g$ was characterized by DSC and DDSC, wherein $T_g$ was located as the peak in the slope of the DSC curve. The results indicated that as the amount of D,L-lactide in the prepolymer increased. $T_g$ increased accordingly (30:70, −36° C.; 50:50, −20° C. ;70:30, 4° C.; and 90:10, 26° C.). This is due to the chemical structure of D,L-lactide, which bears a methyl side group. As a general rule, any structural feature that reduces chain mobility will increase $T_g$. The methyl side group of the D,L-lactide led to an increase in $T_g$ because of the increase of the steric requirements about the main chain.

The increase in $T_g$ can also be explained by the decrease in ε-CL content. ε-caprolactone has five methylene groups, which can act as soft segments in the co-polymer chain. With the decrease in ε-CL content, the mobility imparted to the polymer chain by the methylene groups is decreased too. The star-co-polymer thus has a higher glass transition temperature as D,L-lactide content increases.

As $T_g$ increased almost linearly with the increase in D,L-lactide content, changing monomer composition is a very effective way to manipulate the thermal properties of the star-co-polymer.

Melting Temperatures ($T_m$)

The DSC thermograms did not indicate any melting temperatures for the polymers, as expected, confirming that all the star-co-polymers were amorphous.

Crosslinking Conditions

To prepare the elastomer, several crosslinking conditions were tried. First was to crosslink the star-co-polymer using only BCP (BCP purity was confirmed with DSC and FT-IR). As BCP had a fairly high melting temperature of around 210° C., the crosslinking temperature was raised up to 220° C. This high temperature led to thermal decomposition of the star-co-polymer, and the product after crosslinking was found to be dark yellow in colour.

Secondly, the crosslinking temperature was reduced to 160° C. by adding ε-caprolactone to dissolve BCP. The amount of ε-caprolactone added was two times the weight of BCP, and BCP dissolved at 160° C. But at this temperature, a good elastomer could not be formed because ε-caprolactone partly evaporated, producing samples with a lot of bubbles.

Finally, the crosslinking temperature was brought down to 140° C., and ε-caprolactone was added in a 2:1 ratio to BCP. At this temperature, good samples were prepared which were slightly white in colour and had no bubbles. This indicated that there was no thermal decomposition of the star-co-polymer or evaporation of ε-caprolactone at this temperature.

(B) Characterization of Elastomers

Swelling Tests

Swelling tests were performed on the crosslinked elastomers, and the results indicated that sol-content (i.e, the portion of elastomer that had no covalent bonds to any other chains in the network) ranged from 13.1% to 31.7%, as listed in Table 5. As can be seen from the results, sol-content increased as prepolymer molecular weight increased. Although the swelling test results showed relatively high sol-contents, a true elastomer network was formed, as none of the elastomers dissolved in dichloromethane (DCM), and each kept its original physical structure after DCM was evaporated.

TABLE 5

Swelling test results (n = 3 samples for each elastomer).

| DLL:ε-CL, Mw/arm | Avg. Sol-content (%) | Standard deviation |
| --- | --- | --- |
| 50:50, 900 | 17.9 | 1.1 |
| 50:50, 1350 | 18.8 | 0.81 |
| 50:50, 1800 | 29.2 | 0.62 |
| 50:50, 2700 | 31.7 | 0.55 |
| 30:70, 900 | 13.1 | 3.23 |
| 70:30, 900 | 16.1 | 0.11 |
| 90:10, 900 | 17.7 | 0.29 |
| 90:10, 1800 | 22 | 0.44 |

Glass Transition Temperature

DSC was run on all elastomers to determine the effects of prepolymer molecular weight and monomer composition on the thermal properties of the elastomers.

Influence of Molecular Weight on Glass Transition Temperature

All elastomers were amorphous and had $T_g$s below room temperature. As molecular weight of the prepolymers increased, $T_g$ of the elastomers also increased, which followed the same trend as that of the prepolymers. The elastomers had $T_g$s of −30, −23, −22, and −18° C. for 50:50 polymers of molecular weights of 900, 1350, 1800, and 2700 g/mol per arm, respectively. Theoretically, $T_g$ of a crosslinked elastomer should be higher than that of a prepolymer, because covalent bonds are formed after crosslinking. Crosslinking provides anchoring points for the chains and these anchor points retrain excessive movement and maintain the position of the chain in the network. The decrease in glass transition temperature after crosslinking reported herein was due to ε-caprolactone being added before crosslinking, to dissolve BCP, which was the crosslinker. ε-caprolactone contributed to the softness of the elastomers, and thus resulted in lower glass transition temperatures.

The above result of decreasing $T_g$ of elastomer with decreasing molecular weight of prepolymer indicates that thermal properties of the elastomer can be controlled by controlling the properties of the prepolymer.

Influence of Monomer Composition on Glass Transition Temperature

Thermal analysis indicated that the glass transition temperature of the elastomers could also be manipulated by the monomer composition ratio in the prepolymer synthesis. The elastomers were all amorphous, and had $T_g$s of −40° C. for 30:70 DLL:ε-CL, −30° C. for 50:50 DLL:ε-CL, −20° C. for 70:30 DLL:ε-CL, and −11° C. for 90:10 DLL:ε-CL. The elastomers had lower $T_g$s than the prepolymers due to the effect of ε-caprolactone being added as a solvent to dissolve BCP. Poly (ε-caprotactone) has a $T_g$ of −60° C., and the addition of ε-caprolactone increased the ε-CL content of the material, thus decreasing the $T_g$ of the elastomers.

Tensile Tests

Tensile tests were performed on the crosslinked elastomers to determine the effects of prepolymer molecular weight and monomer composition on the mechanical properties of the elastomers.

Influence of Molecular Weight on Mechanical Properties

Table 6 lists the maximum stress, maximum strain, and Young's modulus of the 50:50 DLL:ε-CL elastomers prepared from prepolymers of different molecular weights. The stress-strain data indicate that the ultimate network strength was reduced by increasing the molecular weight of the prepolymer, whereas ductility was increased by the increase in molecular weight. This can be explained by the decrease in crosslinking density with the increase in molecular weight. A lower crosslinking density allows the network to be stretched more easily, and thus results in a decrease in maximum stress. With the decrease in crosslinkng density, restriction between polymer chains is decreased. The chains become more flexible, and a higher maximum strain can be obtained. The decrease in Young's modulus indicates that the polymer is more elastic, which results from decreasing crosslinking density with increasing molecular weight of the prepolymer.

TABLE 6

Stress-strain data for elastomers prepared from prepolymers of different molecular weights.

| DLL:ε-CL, (MW/arm) | Max. Stress (MPa) | Max. Strain (%) | Young's Modulus (MPa) |
| --- | --- | --- | --- |
| 50:50, 900 | 0.839 | 120 | 0.0070 |
| 50:50, 1350 | 0.766 | 171 | 0.0045 |
| 50:50, 1800 | 0.695 | 260 | 0.0026 |
| 50:50, 2700 | 0.621 | 310 | 0.0020 |

Influence of Monomer Composition on Mechanical Properties

Stress-strain data for elastomers prepared from prepolymers of different monomer composition ratios (DLL:ε-CL) are shown in Table 7. Results indicate that both maximum stress and maximum strain increase as the amount of D,L-lactide in the prepolymer increases.

TABLE 7

Stress-strain data for elastomers prepared from prepolymers of different DLL:ε-CL ratios.

| DLL:ε-CL, (MW/arm) | Max. Stress (MPa) | Max. Strain (%) | Young's Modulus (MPa) |
| --- | --- | --- | --- |
| 30:70, 900 | 0.812 | 92 | 0.0088 |
| 50:50, 900 | 0.839 | 120 | 0.0070 |
| 70:30, 900 | 1.041 | 150 | 0.0069 |
| 90:10, 900 | 1.259 | 186 | 0.0067 |

Example 6

Biocompatibility of Thermally Crosslinked Elastomer

In use of a biodegradable elastomer, such as in the above examples, in applications such as scaffolds in tissue engineering, the rate and extent of initial cell infiltration into the elastomer is important in determining the utility of the material. Accordingly, short term toxicity assays of the material are necessary. Polymers prepared from D,L-lactide and ε-caprolactone and co-polymers of these monomers have been demonstrated to be biocompatible and are used in FDA-approved devices, but little information exists for the toxicity of the BCP crosslinker. BCP was first proposed for use in preparing elastomers of biodegradable polycaprolactone by Pitt et al. (*J. Control Rel.* 1:3–14, 1984), who noted that at 14 and 28 days post-implantation in rat, host reaction to the elastomers was minimal. No other toxicity information was provided.

Method

50:50 poly star co-polymer (SCP) of caprolactone and D,L-lactide was prepared as described in Example 1, and purified by precipitation from dichloromethane (DCM) solution into cold methanol.

An elastomer slab was prepared by compression molding in a Teflon mold (7.5 cm×11 cm×3 mm). In a flame-dried vacuum ampoule, 5 g of BCP was dissolved in 1 g of ε-CL monomer at 140° C. for 15 minutes under a nitrogen blanket. 15 g of molten SCP (140° C.) and an amount of SnOct equivalent to 1.4 ($10^{-4}$) mol for each 1 mol of the SCP prepolymer were added to the ampoule which was then mixed by vortexing. The ampoule was replaced in the oven for 5 minutes under a mild vacuum of 10 mm Hg, to draw out entrapped air. The contents of the ampoule were then poured into a pre-heated Teflon slab mold, taking care not to introduce air bubbles, covered with an additional sheet of Teflon, and allowed to cure for 18 hours at 140° C. After curing, the elastomer sheet was removed using sterile surgical gloves and heat-sealed in sterile aluminum pouches for storage. The polymer was sterilized by $Co^{60}$ irradiation at a dose level of 50 kGy.

Compatibility Studies

All compatibility studies were carried out by Toxikon Inc., Bedford, Mass.

In Vitro Cytotoxicity

The biological reactivity of a mammalian monolayer of L929 mouse fibroblast cells to leachate extracts of the elastomer was determined as outlined in ISO 10993-5, 1999, as follows. L929 cells were incubated in 6-well plates at 2 ml per well (seeded at 2(10–5) cells/well) for 24 hours at 37±1° C. for 24 hours in a humidified atmosphere containing 5±1% $CO_2$. Sterilized and clean polymer slabs (2.1 cm thick, 4.8 cm wide, and 2.9 cm long) were immersed in 10 ml Eagle's minimum essential medium, which also contained 0.25% trypsin, for 24 hours at 37±1° C. for 24 hours in a humidified atmosphere containing 5±1% CO2 to prepare the test article extraction medium. After extraction, the pH of the extraction medium was checked to determine if it had been altered from 7.2. Extraction mediums of a positive control (natural rubber), a negative control (negative control plastic), and a cell medium only control, were prepared in the same manner. The extracts were used to replace the maintenance medium of the cell culture. All cultures were incubated in triplicate for 48 hours for 24 hours at 37±1° C. for 24 hours in a humidified atmosphere containing 5±1% $CO_2$. At time frames of 0, 24, and 48 hours, the cultures were examined for biological reactivity, as indicated by cellular degeneration and malformation. Biological reactivity was rated on a scale from Grade 0 (no reactivity) to Grade 4 (severe reactivity).

Intracutaneous Extract Injection

Local response of an intracutaneous injection of a leachate extract of the elastomer in rabbits was determined by following ISO 10993-10, 1995. New Zealand White rabbits (2 male and 1 female) were acclimatized for a minimum of 5 days prior to the test. Sterilized and clean polymer slabs (2 cm thick, 5 cm wide, and 5.6 cm long) were immersed in 20 ml of either 0.9% USP sodium chloride for injection or cottonseed oil for 24 hours at 37±1° C. A volume of 0.2 ml of each test article was injected intracutaneously at 5 sites on one side of the shaved dorsal area of the three test animals. At 5 other sites on the other side of each rabbit, 0.2 ml of a control consisting of 0.9% USP sodium chloride for injection or cottonseed oil was injected. Prior to testing, the shaved areas of the rabbits were examined and found to be free of mechanical trauma and/or irritation. The injected sites were examined at 24, 48, and 72 hours post-inoculation for gross evidence of tissue reaction, such as erythema, edema, and necrosis, Each site was subjectively scored, and a Primary Irritation Index was calculated by averaging the scores for each of the test article and control extracts for each of the three individual animals. This total was divided by 15 and the control score then subtracted from the test article score. The values thus obtained for each animal were then added and the sum divided by 3.

Systemic Extract Injection

The systemic response of mice to leachate extracts of the elastomer was determined as outlined in ISO 10993-12, 1996. 20 ICR male mice were acclimatized for 5 days prior to testing. Extracts were prepared in the same manner as was done for the Intracutaneous Injection study. The test article extracts were injected intravenously (0.9% USP sodium chloride for injection) and intraperitoneally (cottonseed oil) at a dose of 50 ml/kg, in groups of 5 mice. Similarly, groups of 5 mice were injected with the control vehicles. The animals were observed for 72 hours post inoculation for signs of biological reactivity, such as lethargy, convulsions, hyperactivity, body weight loss, piloerection, and death.

Implantation Test

Tissue reaction to the presence of the solid elastomer was determined as outlined in ISO 10993-6, 1995. Three healthy New Zealand white rabbits, each weighing at least 2.5 kg, were acclimatized for 5 days prior to testing. On the day of testing, the implant sites were clipped so as to be free of fur. The animals were anaesthetized and 5 slabs of the elastomer (of dimensions 1mm×1 mm×10 mm) sterilized in 70 v/v % ethanol were implanted aseptically into the paravertebral muscles using a sterile hypodermic needle. Similarly, 5 strips of a Negative Control Plastic of the same dimensions were also implanted but on the opposite side of the animal. The animals were maintained for a period of 14 days, and then humanely euthanized. After allowing sufficient time that bleeding would not occur post-mortem, the test article sites and the control article sites were removed from the muscle tissue by carefully slicing around the implant site with a scalpel and lifting out the tissue with forceps. A macroscopic evaluation of the excised tissue was done prior to fixation, in which the sites were examined visually via a magnifying lens for inflammation, necrosis, encapsulation, hemorrhage, and discoloration, The excised tissue was fixed in formalin, processed histologically and examined microscopically by a pathologist. The effects of the articles on the tissue were graded using the following scale: 0=normal, 0.5=very slight, 1=slight, 2=moderate, and 3=severe. Effects examined were inflammation (polymorphonuclear cells, lymphocytes. eosinophils, plasma cells, macrophages, giant cells), fibrosis, fatty infiltrate, hemorrhage, necrosis, degeneration, foreign debris, and relative size of the involved area. A Nominal Total Score for the test and control sites for each animal was determined by dividing the mean score of all the sites for each animal (total score divided by the 13 categories of reactions) by the total number of sites examined. This average score was multiplied by 4 to yield a Nominal Total Score for four test and four control sites. The difference between the Nominal Total Scores for the test article and the control article implant sites was used to determine the Overall Toxicity Rating of the test article.

Results

In the preparation of BCP a number of solvents and reactants are used. These compounds include acetic acid, benzene, heptanone, dichloromethane, and m-chloroperoxybenzoic acid. Extensive efforts were taken to remove these compounds from the final product, but the presence of even trace amounts could result in toxicity of the final elastomer product. These compounds could potentially be leached out of the elastomer and be a cause of biological incompatibility.

As a first indication of possible leachate toxicity, a cytotoxicity study was done using L929 mouse fibroblast cells. This test is sensitive, relatively inexpensive and quick to conduct. The elastomer test article was immersed in the cell culture medium at 37° C. for 24 hours and the medium was then used to replace the culture medium of a monolayer of cells and the cells were monitored for 48 hours. After the leaching step, the pH of the extract medium was measured and found to be unaltered from the original pH of 7.2. Cell condition was subjectively assayed in terms of reactivity to the extract medium as either 0 for no reactivity, to 4 for severe reactivity. Severe reactivity is the situation in which there Is nearly complete destruction of the cell layers. These scores were then compared to both a positive and a negative control, as well as a cell culture medium control. There was no sign of cell reactivity to the extract medium over the 48 hour observation time frame. The same result was noted for both the medium and the negative control, while the positive control showed a severe reaction at 24 and 48 hours.

The elastomer was then tested for leachate toxicity in an in vivo setting, by examining both intracutaneous injection for the evaluation of local skin responses and systemic injection for the evaluation of acute systemic toxicity. In these studies, the elastomer test article was extracted in both normal saline for injection and cottonseed oil, to determine if either hydrophilic or hydrophobic leachates are present that may produce a toxic response. The responses of the animals were again subjectively scored and compared to controls consisting of the injection vehicles themselves.

In the intracutaneous testing, none of the test rabbits exhibited any irritation response (erythema, edema, or necrosis) to the extract from the elastomer test article that was greater than that exhibited by the injection vehicles. The Primary Irritation Index for both the saline and cottonseed oil extracts was 0. In every case, the rabbits were observed to remain healthy and they all gained weight. The elastomer test article can therefore be considered a negligible intracutaneous irritant.

The results of the systemic toxicity testing indicated that none of the animals exhibited any signs of systemic toxicity to the extract injection medium over the 3 day observation period. The average score for each time period was zero, and every mouse gained weight at a comparable rate as the control animals. The elastomer test article can therefore be classed as a negligible systemic toxicity threat, for the conditions studied.

Finally, a two week implantation study was undertaken to assess biocompatibility of the elastomer test article in contact with living tissue. After excision of the test article, the excision sites were macroscopically examined for signs of inflammation, encapsulation, hemorrhage, necrosis and discoloration and these examinations compared to those of a negative control. It was observed that the test article and control sites had no inflammation or other signs of biological reaction. Microscopic evaluation of the elastomer test article did not show any increase in biological reactivity as compared to the control article sites after the 14 day period. The Toxicity Rating (average of the three animals) of the test article was 0.41, which indicates no toxicity.

Conclusion

It is concluded that, under the conditions examined, the leachate of the elastomer material does not exhibit any cytotoxicity, is not locally irritating, and does not exhibit any signs of systemic toxicity. This finding means that the method used to prepare the material does not leave any toxic compounds within the material. The implantation study shows that the elastomer material is not toxic after two weeks in the body. However, preliminary in vitro studies show that the elastomer material does not significantly degrade until about 4 months in PBS buffer; thus, possible toxicity as a result of degradation products has not been completely assessed. Nevertheless, previous work by Pitt and coworkers (*J. Control. Rel.* 1:3–14, 1984) using the same crosslinking compound demonstrated no adverse long-term tissue response. It is therefore expected that the elastomer of the invention will have no toxicity as it degrades.

Example 7

Drug Delivery (A) Bupivacaine-loaded Elastomer

Drug-loading was achieved by soaking an elastomer prepared from a 30:70 (DLL:ϵ-CL) BCP crosslinked 2700 g/mol prepolymer (see Examples 1 and 5) in a solution consisting of 0.125 mg bupivacaine HCl in 90 ml of 4:5 acetone:dichloromethane (vol:vol). The elastomer was soaked in this solution (which swells the elastomer but does not dissolve it) for 24 hours, and the elastomers were then dried for 24 hours.

Figure 12:
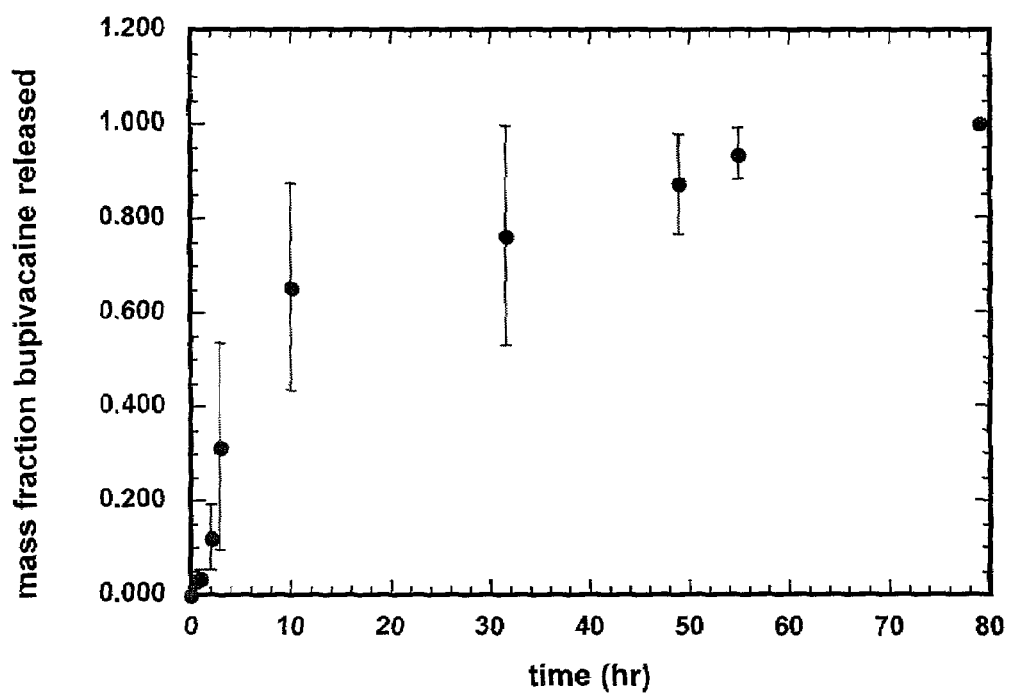
FIG. 12 is a plot of the mass fraction of bupivicaine released into distilled water from a bupivicain-loaded elastomer as a function of time.

A release study was performed using distilled water, The bupivacaine-loaded elastomer was cut into slabs (1 cm×1 cm×3 mm) and slabs were placed into 25 ml glass scintillation vials, which were filled with 20 ml distilled water. The vials were placed in a shaking bath maintained at 37° C., At each sampling period, the slabs were removed and placed in a new scintillation vial containing 20 ml of fresh distilled water The amount of bupivacaine HCl in the distilled water was measured by UV absorbance at 260 nm and the concentration obtained by comparison to a calibration curve. The average(n=3) mass fraction of bupivacaine released as a function of time is shown in FIG. 12, wherein it can be seen that approximately all of the bupivacaine had been released after 80 hours.

(B) Pilocarpine Nitrate-loaded Elastomer

A 50% by weight solution of acrylated SCP was prepared using dichloromethane (DCM) as the solvent (see Example 2) and a quantity of 30 w/v % 2,2-dimethoxy-2-phenyl acetophenone was added (30 µl per 1 ml of SCP solution). To this solution was added pilocarpine nitrate solid particles which had been sieved to have an average particle size of 45 µm. The particles were suspended in the SCP solution by vortexing for 3 minutes. After vortexing, the suspension was poured into a glass tube (3 mm diameter) and immediately exposed to a UV lamp (see Example 2) at a distance of 5 cm for 10 minutes. The DCM was allowed to evaporate and the drug-loaded elastomer cylinders were removed from the glass tubing. The cylinders were then cut into lengths of 1 or 2 cm. Cylinders having 2.5% and 5% by weight loading were prepared.

In some cases, trehalose was also added to the pilocarpine nitrate polymer solution suspension. The trehalose was also sieved to an average diameter of 45 µm, intimately mixed with the pilocarpine nitrate solids, and then suspended in the SCP solution. Crosslinking to form an elastomer was performed as described above. In this way, elastomer cylinders were prepared which contained 2.5 w/w % pilocarpine nitrate and 2.5 w/w % trehalose.

The drug-loaded elastomer cylinders were placed in 50 ml glass tubes filled with either isotonic phosphate buffered saline (pH 7.4), distilled water, or 3% NaCl dissolution medium which had been pre-heated to 37° C. The tubes were then placed on a rotary shaker which was housed in an oven maintained at 37° C. At frequent sampling times, the release medium was sampled. and replaced with fresh medium. The sampled release medium was assayed for pilocarpine nitrate using UV absorbance at 215 nm and the concentration obtained by comparison to a calibration curve.

Figure 13A:
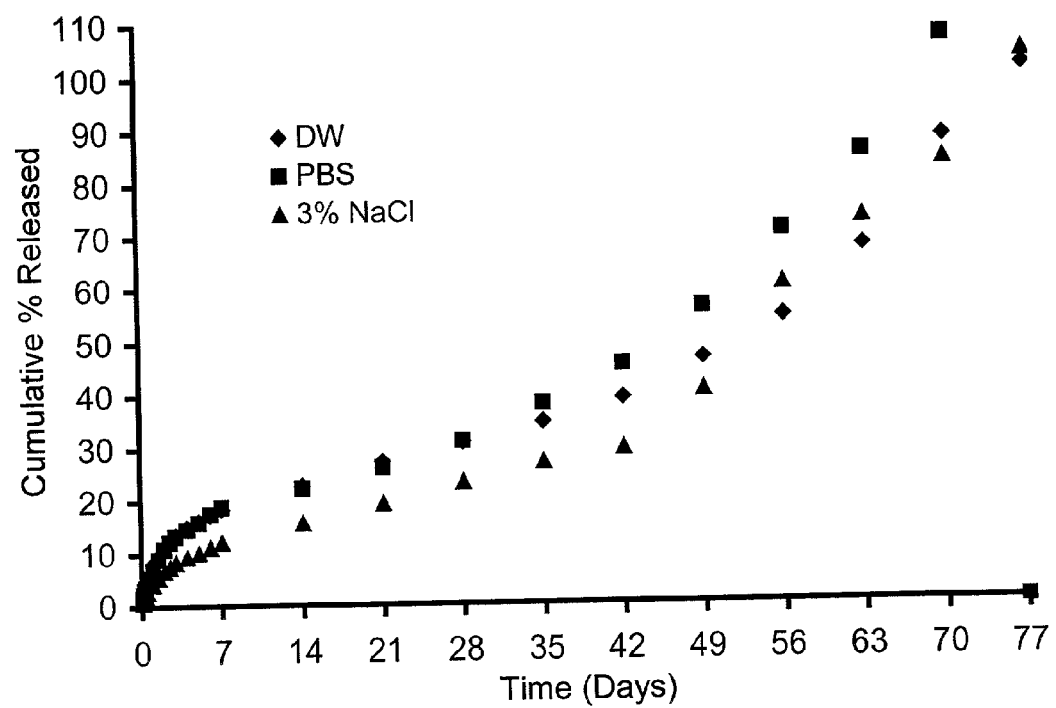
FIGS. 13A and 13B show cumulative % pilocarpine released from 2.5% and 5% loaded elastomer, respectively, in distilled water, PBS, and 3% NaCl dissolution media.
Figure 13B:
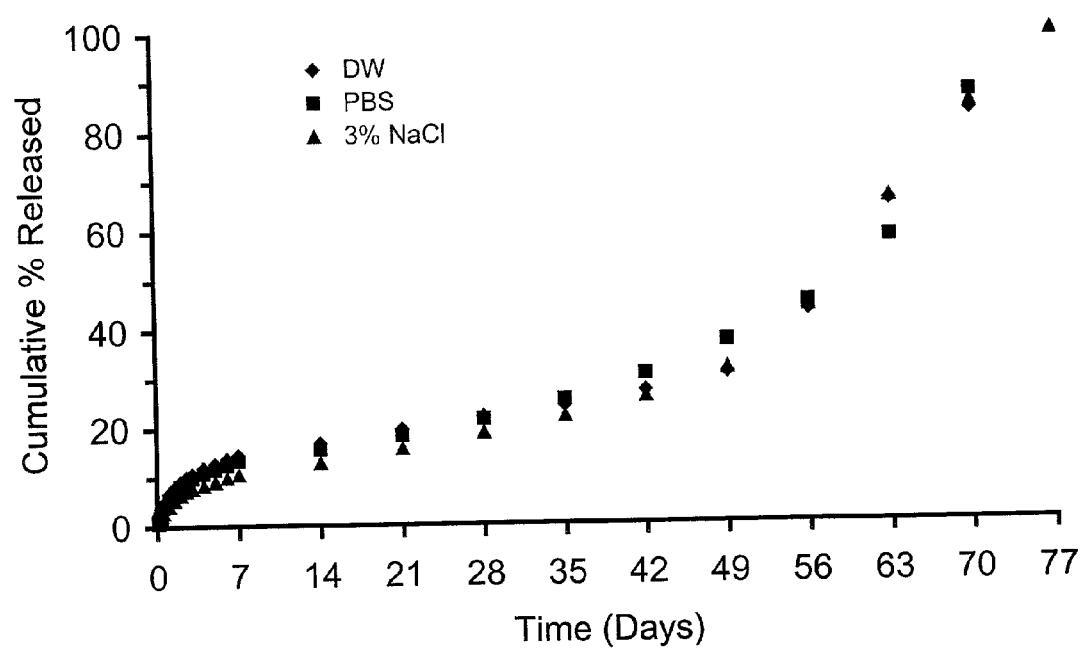
Figure 13C:
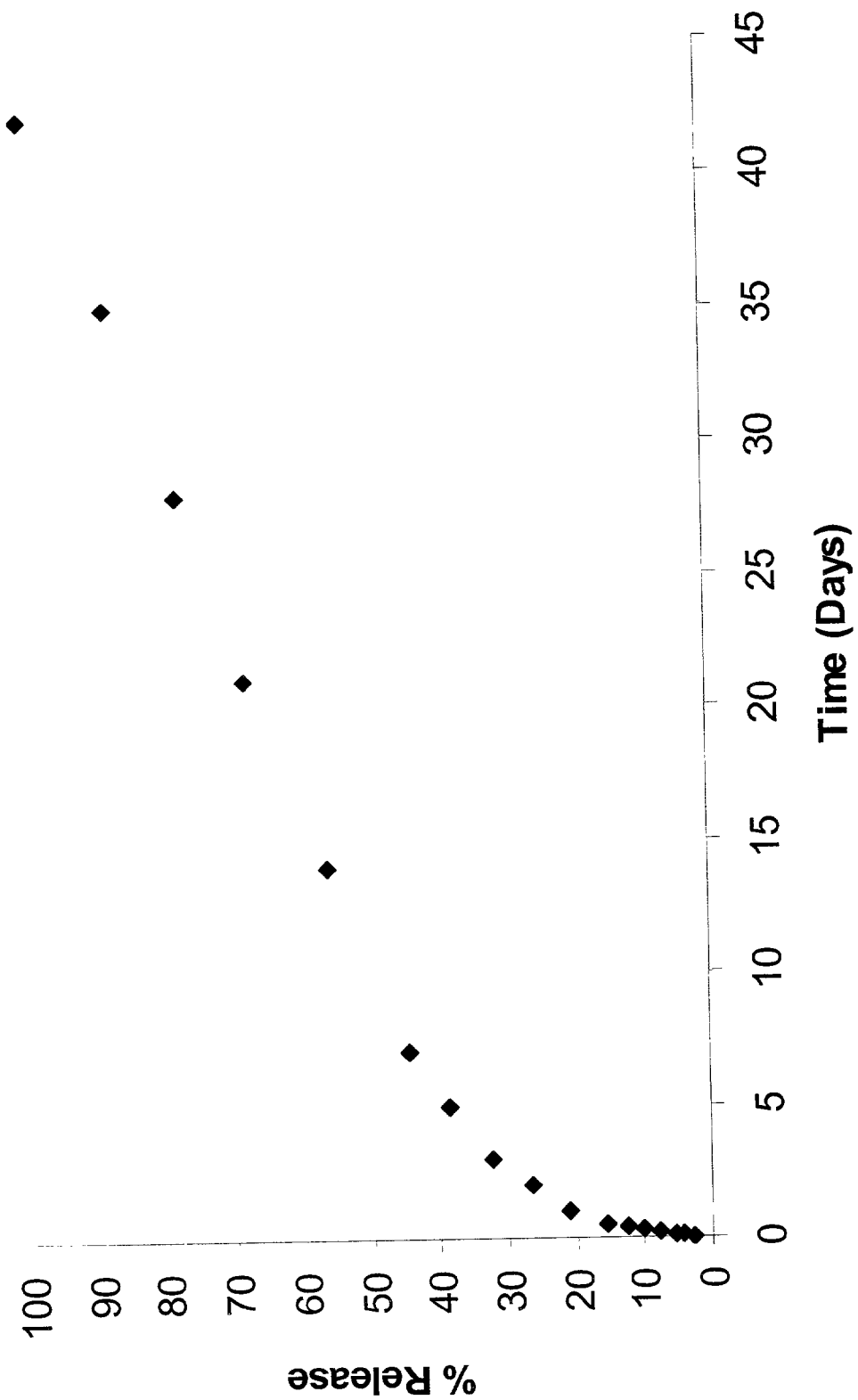
FIG. 13C shows cumulative % pilocarpine released for 2.5% pilocarpine with 2.5% trehalose loaded elastomer in PBS.

FIGS. 13A and 13B show cumulative % pilocarpine nitrate released from 2.5% and 5% loaded cylinders, respectively, in distilled water, PBS, and 3% NaCl dissolution media. FIG. 13C shows cumulative % pilocarpine released for 2.5% pilocarpine with 2.5% trehalose loaded cylinders in PBS. It can be seen that for the 2.5% and 5% loaded cylinders, the release profile was similar for the three dissolution media, and approximately 100% of the pilocarpine was released after 70 to 77 days. The rate of release was faster for the pilocarpine/trehalose cylinder, with approximately 100% of the pilocarpine being released after about 100 hours (42 days).

(C) Osmotic Protein Delivery

Trehalose was lyophilized with interferon gamma at a ratio of 1:1 with succinate buffer at pH 5.5. To prepare the lyophilized protein, the excipient was added as a solid to aliquots of the protein solution and stirred gently at room temperature until dissolved. The solution was then filtered with a 0.22 µm low protein binding filter to remove any particulates. The filtered solution was subjected to a cycle of freezing to –55° C. in dry ice, primary drying at –10° C. and 120 mTorr for 22 hours, followed by secondary drying at 5° C. and 120 mTorr for 12 hours to obtained the dried lyophilized product.

To provide good encapsulation efficiencies, a suspension of the lyophilized protein/excipient solids, which had been sieved to <10 µm, was prepared in a solution of polymer and dichloromethane containing the photo-initiator (see Examples 2 and 5). This suspension was poured into a glass cylinder (e.g., a glass pipette, 1 mm dia., 1 cm long), sealed at each end, and then exposed to UV radiation as described above. for 1 to 2 minutes, to crosslink the elastomer. After crosslinking, the glass cylinder was broken and the drug-loaded cylinder removed. To avoid any settling of the protein particles, the amount of dichloromethane added was kept to the minimal amount required. The small size of the protein particles also assisted in retarding the settling rate.

A release study was conducted as follows: Drug-loaded elastomer cylinders were placed in 50 ml glass tubes filled with isotonic phosphate buffered saline (pH 7.4) which had been pre-heated to 37° C. The tubes were then placed on a rotary shaker which was housed in an oven maintained at 37° C. At frequent sampling times, the release medium was sampled, and replaced with fresh medium. Interferon gamma activity was determined using ELISA. Results to date indicate that after 15 days, activity of interferon gamma was the same as that for interferon gamma as received from the supplier. It is expected that this represents about 50% of the initially incorporated material. Further analyses are currently in progress.

Equivalents

Those skilled in the art will recognize variants of the embodiments described herein and presented in the above Examples, Such variants are intended to be within the scope of the invention and are covered by the appended claims.

I claim:

1. A method of preparing a thermally crosslinked biodegradable/biocompatible elastomeric polymer comprising:
   combining a star co-polymer with a bis-lactone crosslinking agent, and
   heating the combined star co-polymer and crosslinking agent,
   so that a crosslinked biodegradable/biocompatible elastomeric polymer is prepared.

2. The method of claim 1, wherein the star co-polymer comprises at least one monomer, said at least one monomer capable of forming a biodegradable linkage to another monomer.

3. The method of claim 2, wherein the monomer is capable of undergoing ring-opening polymerization.

4. The method of claim 1, wherein the star co-polymer further comprises an initiator.

5. The method of claim 2, wherein said at least one monomer is a member of a group selected from lactones, carbonates, and cyclic amides.

6. The method of claim 2, wherein said at least one monomer is selected from valerolactone, ε-caprolactone, dioxepanone, lactide, glycolide, trimethylene carbonate, and O-benzyl-L-serine.

7. The method of claim 4, wherein the initiator is a polyol.

8. The method of claim 7, wherein the polyol is selected from glycerol, pentaerythritol, and xylitol.

9. The method of claim 1, wherein the star co-polymer has a glass transition temperature ($T_g$) below room temperature and is amorphous.

10. The method of claim 1, wherein the star co-polymer is a lactone star co-polymer.

11. The method of claim 10, wherein the lactone star co-polymer comprises ε-caprolactone and D,L-lactide.

12. The method of claim 11, wherein the molar ratio of ε-caprolactone and D,L-lactide is from about 10:90 to about 90:10.

13. The method of claim 1, wherein the bis-lactone crosslinking agent is (2,2-)bis(ε-caprolactone-4-yl)propane (BCP).

14. A method of preparing an amorphous photo-crosslinked biodegradable/biocompatible elastomeric polymer comprising:
   combining an amorphous photo-crosslinkable star co-polymer with an initiator, and
   exposing the combined star polymer and initiator to photo-crosslinking light;
   so that an amorphous crosslinked biodegradable/biocompatible elastomeric polymer is prepared.

15. The method of claim 14, wherein the star co-polymer comprises at least one monomer, said at least one monomer capable of forming a biodegradable linkage to another monomer.

16. The method of claim 15, wherein the monomer is capable of undergoing ring-opening polymerization.

17. The method of claim 14, wherein the star co-polymer further comprises one or more photo-crosslinkable groups on the polymer chain termini.

18. The method of claim 15, wherein said at least one monomer is a member of a group selected from lactones, carbonates, and cyclic amides.

19. The method of claim 15, wherein said at least one monomer is selected valerolactone, ε-caprolactone, dioxepanone, lactide, glycolide, trimethylene carbonate, and O-benzyl-L-serine.

20. The method of claim 17, wherein the photo-crosslinkable group is selected from acrylate, coumarin, thymine, cinnamates, diacrylates, oligoacrylates, methacrylates, dimethacrylates, and oligomethacrylates.

21. The method of claim 17, wherein the initiator absorbs photons to form a free radical which reacts with an allyl group of the photo-crosslinkable group.

22. The method of claim 21, wherein the initiator is selected from acetophenone derivatives, camphorquinone, Irgacure® (1-hydroxy-cyclohexyl-phenyl-ketone, 1-[4-(2-hydroxyethoxy)-phenyl]-2-hydroxy-2-methyl-1-propane-1-one, 2,2-dimethoxy-1,2-diphenylethan-1-one, or 2-methyl-1[-4-(methylthio) phenyl]-2-(4-morpho-linyl)-1-propanone), Darocur® (1-[4-(2-hydroxyethoxy)-phenyl]-2-hydroxy-2-methyl-1-propane-1-one or 2,4,6-trimethylbenzoyl-diphenyl-phosphineoxide), and eosin dye.

23. The method of claim 22, wherein the initiator is selected from 2,2-dimethyl-2-phenylacetaphenone and 2-methoxy-2-phenylacetaphenone.

24. A thermally crosslinked biodegradable/biocompatible elastomeric polymer prepared according to claim 1.

25. A photo-crosslinked biodegradable/biocompatible elastomeric polymer prepared according to claim 14.

26. A device comprising a biodegradable/biocompatible elastomeric polymer according to claim 24.

27. The device of claim 26, wherein said device is a biomedical device selected from a needle, a stent, a catheter, and a scaffold.

28. A device comprising a biodegradable/biocompatible elastomeric polymer according to claim 25.

29. The device of claim 28, wherein said device is a biomedical device selected from a needle, a stent, a catheter, and a scaffold.

30. An implantable drug delivery device comprising a biodegradable/biocompatible elastomeric polymer according to claim 24, and a pharmaceutical agent.

31. The device of claim 30, wherein the pharmaceutical agent is a protein or a peptide.

32. The device of claim 30, further comprising an excipient.

33. An implantable drug delivery device comprising a biodegradable/biocompatible elastomeric polymer according to claim 25, and a pharmaceutical agent.

34. The device of claim 33, wherein the pharmaceutical agent is a protein or a peptide.

35. The device of claim 33, further comprising an excipient.

36. The thermally crosslinked biodegradable/biocompatible elastomeric polymer of claim 24, wherein the star co-polymer comprises at least one monomer, said at least one monomer capable of forming a biodegradable linkage to another monomer.

37. The thermally crosslinked biodegradable/biocompatible elastomeric polymer of claim 24, wherein the star co-polymer is capable of undergoing ring-opening polymerization.

38. The thermally crosslinked biodegradable/biocompatible elastomeric polymer of claim 24, wherein the star co-polymer further comprises an initiator.

39. The thermally crosslinked biodegradable/biocompatible elastomeric polymer of claim 38, wherein the initiator is a polyol.

40. The thermally crosslinked biodegradable/biocompatible elastomeric polymer of claim 39, wherein the polyol is selected from glycerol, pentaerythritol, and xylitol.

41. The thermally crosslinked biodegradable/biocompatible elastomeric polymer of claim 36, wherein said at least one monomer is a member of a group selected from lactones, carbonates, and cyclic amides.

42. The thermally crosslinked biodegradable/biocompatible elastomeric polymer of claim 36, wherein said at least one monomer is selected from valerolactone, ϵ-caprolactone, dioxepanone, lactide, glycolide, trimethylene carbonate, and O-benzyl-L-serine.

43. The thermally crosslinked biodegradable/biocompatible elastomeric polymer of claim 24, wherein the star co-polymer has a glass transition temperature ($T_g$) below room temperature and is amorphous.

44. The thermally crosslinked biodegradable/biocompatible elastomeric polymer of claim 24, wherein the star co-polymer is a lactone star co-polymer.

45. The thermally crosslinked biodegradable/biocompatible elastomeric polymer of claim 44, wherein the lactone star co-polymer comprises ϵ-caprolactone and D,L-lactide.

46. The thermally crosslinked biodegradable/biocompatible elastomeric polymer of claim 45, wherein the molar ratio of ϵ-caprolactone and D,L-lactide is from about 10:90 to about 90:10.

47. The thermally crosslinked biodegradable/biocompatible elastomeric polymer of claim 24, wherein the bis-lactone crosslinking agent is (2,2-)bis (ϵ-caprolactone-4-yl) propane (BCP).

48. The photo-crosslinked biodegradable/biocompatible elastomeric polymer of claim 25, wherein the star co-polymer comprises at least one monomer, said at least one monomer capable of forming a biodegradable linkage to another monomer.

49. The photo-crosslinked biodegradable/biocompatible elastomeric polymer of claim 25, wherein the star co-polymer is capable of undergoing ring-opening polymerization.

50. The photo-crosslinked biodegradable/biocompatible elastomeric polymer of claim 25, wherein the star co-polymer further comprises one or more photo-crosslinkable groups on the polymer chain termini.

51. The photo-crosslinked biodegradable/biocompatible elastomeric polymer of claim 48, wherein said at least one monomer is a member of a group selected from lactones, carbonates, and cyclic amides.

52. The photo-crosslinked biodegradable/biocompatible elastomeric polymer of claim 48, wherein said at least one monomer is selected from valerolactone, ϵ-caprolactone, dioxepanone, lactide, glycolide, trimethylene carbonate, and O-benzyl-L-serine.

53. The photo-crosslinked biodegradable/biocompatible elastomeric polymer of claim 50, wherein the photo-crosslinkable group is selected from acrylate, coumarin, thymine, cinnamates, diacrylates, oligoacrylates, methacrylates, dimethacrylates, and oligomethacrylates.

54. The photo-crosslinked biodegradable/biocompatible elastomeric polymer of claim 50, wherein the initiator absorbs photons to form a free radical which reacts with an allyl group of the photo-crosslinkable group.

55. The photo-crosslinked biodegradable/biocompatible elastomeric polymer of claim 54, wherein the initiator is selected from acetophenone derivatives, camphorquinone, Irgacure® (1-hydroxy-cyclohexyl-phenyl-ketone, 1-[4-(2-hydroxyethoxy)-phenyl]-2-hydroxy-2-methyl-1-propane-1-one, 2,2-dimethoxy-1,2-diphenylethan-1-one, or 2-methyl-1-[4-(methylthio)phenyl]-2-(4-morpho-linyl)-1-propanone), Darocur® (1-[4-(2-hydroxyethoxy)-phenyl]-2-hydroxy-2-methyl-1-propane-1-one or 2,4,6-trimethylbenzoyl-diphenyl-phosphineoxide), and eosin dye.

56. The photo-crosslinked biodegradable/biocompatible elastomeric polymer of claim 55, wherein the initiator is selected from 2,2-dimethyl-2-phenylacetaphenone and 2-methoxy-2-phenylacetaphenone.

* * * * *